United States Patent [19]
Lee et al.

[11] Patent Number: 5,863,727
[45] Date of Patent: Jan. 26, 1999

[54] ENERGY TRANSFER DYES WITH ENHANCED FLUORESCENCE

[75] Inventors: Linda G. Lee, Palo Alto; Sandra L. Spurgeon, San Mateo; Barnett Rosenblum, San Jose, all of Calif.

[73] Assignee: The Perkin-Elmer Corporation, Foster City

[21] Appl. No.: 642,330

[22] Filed: May 3, 1996

[51] Int. Cl.$^6$ ..................................................... C12Q 1/68
[52] U.S. Cl. .............................. 435/6; 536/26.6; 549/223
[58] Field of Search .......................... 536/26.6; 549/223, 549/224, 225, 226, 227; 435/6

[56] References Cited

U.S. PATENT DOCUMENTS

| | | | |
|---|---|---|---|
| 4,996,143 | 2/1991 | Heller et al. | 435/6 |
| 5,188,934 | 2/1993 | Menchen et al. | 435/6 |
| 5,607,834 | 3/1997 | Bagwell | 435/6 |

FOREIGN PATENT DOCUMENTS

| | | |
|---|---|---|
| 0 201 751 A2 | 11/1985 | European Pat. Off. . |
| 0 229 943 A2 | 7/1987 | European Pat. Off. . |
| 0 601 889 A2 | 6/1994 | European Pat. Off. . |
| WO 93/13224 | 7/1983 | WIPO . |
| WO 95/21266 | 8/1995 | WIPO . |

OTHER PUBLICATIONS

Cardullo, et al. "Detection of nucleic acid hybridization by nonradiative fluorescence resonance energy transfer", Proc. Nat. Acad. Sci., vol. 85, pp. 8790–8794 (Dec. 1988).

Clegg, "Fluorescence Resonance Energy Transfer and Nucleic Acids", Methods in Enzymology, vol. 211, pp. 353–388 (1992).

Jue, et al., "Design and Synthesis of Fluorescence Energy Transfer Dye–Labeled Primer and Their Application for DNA Sequencing and Analysis", Analytical Biochemistry, vol. 231, pp. 131–140 (1995).

Jue, et al., "Fluorescnce energy transfer dye–labledd primers for DNA sequencing and analysis", Proc. Natl. Acad. Sci., vol. 92, pp. 4347–4351 (1995).

Lee, et al., "Allelic discrimination by nick–translation PCR with fluorogenic probes", Nucleic Acids Research, vol. 21, No. 16, pp. 3761–3766 (1993).

Llvak, et al., "Oligonucleotides with Fluorescent Dyes at Opposite Ends Provide a Quenched Probe System Useful for Detecting PCR Produces and Nucleic Acid Hybridization", PCR Methods and Applications, pp. 357–362 (1995).

Shipchandler, et al., "4'-[Aminomethyl] fluorescein and Its N–Alkyl Derivatives: Useful Reagents in Immunodiagnostic Techniques", Analytical Biochemistry, vol. 162, pp. 89–101 (1987).

Stryer, et al., "Energy Transfer: A Spectroscopic Ruler", Proc. Nat'l Acad. Sci., pp. 719–726 (1967).

Wu, et al., "Resonance Energy Transfer:Methods and Applications", Analytical Biochemsitry, vol., 218, pp. 1–13 (1994).

Stenzel et al., Clin. Chem. 39(11):228–2232, 1992.

Lee et al., Nucleic Acids Res. 20(10):2471–2483, 1992.

Drake, et al., Science, vol. 251, pp. 1574–1579 (1991).

Cooper, et al., Biochemistry, vol. 29, pp. 9261–9268 (1990).

Ju, et al., PNAS USA 92 4347–4351 (1995).

Tyagi, et al., Nature Biotechnology, vol. 14, pp. 303–308 (1966).

*Primary Examiner*—Scott W. Houtteman
*Attorney, Agent, or Firm*—Wilson Sonsini Goodrich & Rosati

[57] ABSTRACT

Energy transfer fluorescent dyes, reagents incorporating the dyes, kits and methods for using the dyes and reagents are provided. The energy transfer fluorescent dyes include a donor dye which absorbs light at a first wavelength and emits excitation energy in response, the donor dye including a xanthene ring structure having a 4' ring position, an acceptor dye capable of absorbing the excitation energy emitted by the donor dye and fluorescing at a second wavelength in response, and a linker attaching the donor dye to the acceptor dye, the linker having a 4' end which includes a $R_1XC(O)R_2$ group where $R_1$ is a $C_{1-5}$ alkyl attached to the 4' ring position of the donor dye, X selected from the group consisting of NH, sulfur and oxygen, C(O) is a carbonyl group, and $R_2$ includes an alkene, diene, alkyne, a five and six membered ring having at least one unsaturated bond or a fused ring structure which is attached to the carbonyl carbon. Alternatively, the energy transfer fluorescent dyes include a donor dye which absorbs light at a first wavelength and emits excitation energy in response, the donor dye including a xanthene ring structure, an acceptor dye which is either a xanthene, cyanine, phthalocyanine or squaraine dye which is capable of absorbing the excitation energy emitted by the donor dye and fluorescing at a second wavelength in response, the acceptor having an emission maximum that is greater than about 600 nm or at least about 100 nm greater than the absorbance maximum of the donor dye, and a linker attaching the donor dye to the acceptor dye.

59 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 1217 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 1:

| | | | | |
|---|---|---|---|---:|
| GCCAAGCTTG | CATGCCTGCA | GGTCGACTCT | AGAGGATCCC | 40 |
| CGGGTACCGA | GCTCGAATTC | GTAATCATGG | TCATAGCTGT | 80 |
| TTCCTGTGTG | AAATTGTTAT | CCGCTCACAA | TTCCACACAA | 120 |
| CATACGAGCC | GGAAGCATAA | AGTGTAAAGC | CTGGGGTGCC | 160 |
| TAATGAGTGA | GCTAACTCAC | ATTAATTGCG | TTGCGCTCAC | 200 |
| TGCCCGCTTT | CCAGTCGGGA | AACCTGTCGT | GCCAGCTGCA | 240 |
| TTAATGAATC | GGCCAACGCG | CGGGGAGAGG | CGGTTTGCGT | 280 |
| ATTGGGCGCC | AGGGTGGTTT | TTCTTTTCAC | CAGTGAGACG | 320 |
| GGCAACAGCT | GATTGCCCTT | CACCGCCTGG | CCCTGAGAGA | 360 |
| GTTGCAGCAA | GCGGTCCACG | CTGGTTTGCC | CCAGCAGGCG | 400 |
| AAAATCCTGT | TTGATGGTGG | TTCCGAAATC | GGCAAAATCC | 440 |
| CTTATAAATC | AAAAGAATAG | CCCGAGATAG | GGTTGAGTGT | 480 |
| TGTTCCAGTT | TGGAACAAGA | GTCCACTATT | AAAGAACGTG | 520 |
| GACTCCAACG | TCAAGGGCG | AAAAACCGTC | TATCAGGGCG | 560 |
| ATGGCCCACT | ACGTGAACCA | TCACCCAAAT | CAAGTTTTT | 600 |
| GGGGTCGAGG | TGCCGTAAAG | CACTAAATCG | GAACCCTAAA | 640 |
| GGGAGCCCCC | GATTTAGAGC | TTGACGGGGA | AAGCCGGCGA | 680 |
| ACGTGGCGAG | AAAGGAAGGG | AAGAAAGCGA | AAGGAGCGGG | 720 |
| CGCTAGGGCG | CTGGCAAGTG | TAGCGGTCAC | GCTGCGCGTA | 760 |
| ACCACCACAC | CCGCCGCGCT | TAATGCGCCG | CTACAGGGCG | 800 |
| CGTACTATGG | TTGCTTTGAC | GAGCACGTAT | AACGTGCTTT | 840 |
| CCTCGTTGGA | ATCAGAGCGG | GAGCTAAACA | GGAGGCCGAT | 880 |
| TAAAGGGATT | TTAGACAGGA | ACGGTACGCC | AGAATCTTGA | 920 |
| GAAGTGTTTT | TATAATCAGT | GAGGCCACCG | AGTAAAGAG | 960 |
| TCTGTCCATC | ACGCAAATTA | ACCGTTGTAG | CAATACTTCT | 1000 |
| TTGATTAGTA | ATAACATCAC | TTGCCTGAGT | AGAAGAACTC | 1040 |
| AAACTATCGG | CCTTGCTGGT | AATATCCAGA | ACAATATTAC | 1080 |
| CGCCAGCCAT | TGCAACAGGA | AAAACGCTCA | TGGAAATACC | 1120 |
| TACATTTTGA | CGCTCAATCG | TCTGAAATGG | ATTATTTACA | 1160 |
| TTGGCAGATT | CACCAGTCAC | ACGACCAGTA | ATAAAAGGGA | 1200 |
| CATTCTGGCC | AACAGAG | | | 1217 |

( 2 ) INFORMATION FOR SEQ ID NO: 2:

( i ) SEQUENCE CHARACTERISTICS:
        ( A ) LENGTH: 18 nucleotides
        ( B ) TYPE: nucleic acid
        ( C ) STRANDEDNESS: single
        ( D ) TOPOLOGY: linear ( x i ) SEQUENCE DESCRIPTION: SEQ ID NO: 2:

TGTAAAACGA   CGGCCAGT                                                          1 8

ENERGY TRANSFER DYES WITH ENHANCED FLUORESCENCE

BACKGROUND OF THE INVENTION

1. Field of the Invention

The present invention relates to fluorescent dyes and, more specifically, energy transfer fluorescent dyes and their use.

2. Description of Related Art

A variety of fluorescent dyes have been developed for labelling and detecting components in a sample. In general, fluorescent dyes preferably have a high quantum yield and a large extinction coefficient so that the dye may be used to detect small quantities of the component being detected. Fluorescent dyes also preferably have a large Stokes shift (i.e., the difference between the wavelength at which the dye has maximum absorbance and the wavelength at which the dye has maximum emission) so that the fluorescent emission is readily distinguished from the light source used to excite the dye.

One class of fluorescent dyes which has been developed is energy transfer fluorescent dyes. In general, energy transfer fluorescent dyes include a donor fluorophore and an acceptor fluorophore. In these dyes, when the donor and acceptor fluorophores are positioned in proximity with each other and with the proper orientation relative to each other, the energy emission from the donor fluorophore is absorbed by the acceptor fluorophore and causes the acceptor fluorophore to fluoresce. It is therefore important that the excited donor fluorophore be able to efficiently absorb the excitation energy of the donor fluorophore and efficiently transfer the energy to the acceptor fluorophore.

A variety of energy transfer fluorescent dyes have been described in the literature. For example, U.S. Pat. No. 4,996,143 and WO 95/21266 describe energy transfer fluorescent dyes where the donor and acceptor fluorophores are linked by an oligonucleotide chain. Lee, et al., *Nucleic Acids Research* 20:10 2471–2483 (1992) describes an energy transfer fluorescent dye which includes 5-carboxy rhodamine linked to 4'-aminomethyl-5-carboxy fluorescein by the 4'-aminomethyl substituent on fluorescein.

Several diagnostic and analytical assays have been developed which involve the detection of multiple components in a sample using fluorescent dyes, e.g. flow cytometry (Lanier, et al., *J. Immunol.* 132 151–156 (1984)); chromosome analysis (Gray, et al., *Chromosoma* 73 9–27 (1979)); and DNA sequencing. For these assays, it is desirable to simultaneously employ a set of two or more spectrally resolvable fluorescent dyes so that more than one target substance can be detected in the sample at the same time. Simultaneous detection of multiple components in a sample using multiple dyes reduces the time required to serially detect individual components in a sample. In the case of multi-loci DNA probe assays, the use of multiple spectrally resolvable fluorescent dyes reduces the number of reaction tubes that are needed, thereby simplifying the experimental protocols and facilitating the manufacturing of application-specific kits. In the case of automated DNA sequencing, the use of multiple spectrally resolvable fluorescent dyes allows for the analysis of all four bases in a single lane thereby increasing throughput over single-color methods and eliminating uncertainties associated with inter-lane electrophoretic mobility variations. Connell, et al., *Biotechniques* 5 342–348 (1987); Prober, et al., *Science* 238 336–341 (1987), Smith, et al., *Nature* 321 674–679 (1986); and Ansorge, et al., *Nucleic Acids Research* 15 4593–4602 (1989).

There are several difficulties associated with obtaining a set of fluorescent dyes for simultaneously detecting multiple target substances in a sample, particularly for analyses requiring an electrophoretic separation and treatment with enzymes, e.g., DNA sequencing. For example, each dye in the set must be spectrally resolvable from the other dyes. It is difficult to find a collection of dyes whose emission spectra are spectrally resolved, since the typical emission band half-width for organic fluorescent dyes is about 40–80 nanometers (nm) and the width of the available spectrum is limited by the excitation light source. As used herein the term "spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instrumentation and Data Analysis* (Academic Press, N.Y., 1985).

The fluorescent signal of each of the dyes must also be sufficiently strong so that each component can be detected with sufficient sensitivity. For example, in the case of DNA sequencing, increased sample loading can not compensate for low fluorescence efficiencies, Pringle et al., *DNA Core Facilities Newsletter*, 1 15–21 (1988). The fluorescent signal generated by a dye is generally greatest when the dye is excited at its absorbance maximum. It is therefore preferred that each dye be excited at about its absorbance maximum.

A further difficulty associated with the use of a set of dyes is that the dyes generally do not have the same absorbance maximum. When a set of dyes are used which do not have the same absorbance maximum, a trade off is created between the higher cost associated with providing multiple light sources to excite each dye at its absorbance maximum, and the lower sensitivity arising from each dye not being excited at its absorbance maximum.

In addition to the above difficulties, the charge, molecular size, and conformation of the dyes must not adversely affect the electrophoretic mobilities of the fragments. The fluorescent dyes must also be compatible with the chemistry used to create or manipulate the fragments, e.g., DNA synthesis solvents and reagents, buffers, polymerase enzymes, ligase enzymes, and the like.

Energy transfer fluorescent dyes possess several features which make them attractive for use in the simultaneous detection of multiple target substances in a sample, such as in DNA sequencing. For example, a single donor fluorophore can be used in a set of energy transfer fluorescent dyes so that each dye has strong absorption at a common wavelength. Then, by varying the acceptor fluorophore in the energy transfer dye, a series of energy transfer dyes having spectrally resolvable fluorescence emissions can be generated.

Energy transfer fluorescent dyes also provide a larger effective Stokes shift than non-energy transfer fluorescent dyes. This is because the Stokes shift for an energy transfer fluorescent dye is based on the difference between the wavelength at which the donor fluorophore maximally absorbs light and the wavelength at which the acceptor fluorophore maximally emits light. In general, a need exists for fluorescent dyes having larger Stokes shifts.

The sensitivity of any assay using a fluorescent dye is dependent on the strength of the fluorescent signal generated by the fluorescent dye. A need therefore exists for fluorescent dyes which have a strong fluorescence signal. With regard to energy transfer fluorescent dyes, the fluorescence signal strength of these dyes is dependent on how efficiently the acceptor fluorophore absorbs the energy emission of the donor fluorophore. This, in turn, depends on a variety of variables, including the proximity of the donor fluorophore to the acceptor fluorophore and the orientation of the donor fluorophore relative to the acceptor fluorophore. A need therefore exists for energy transfer fluorescent dyes in which the orientation between the donor and acceptor fluorophore is such that energy is efficiently transferred between the donor and acceptor fluorophore.

SUMMARY OF THE INVENTION

The present invention relates to energy transfer fluorescent dyes having enhanced fluorescence which include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye.

In one embodiment of the energy transfer fluorescent dyes, the donor dye has the following xanthene ring structure with a 4' ring position

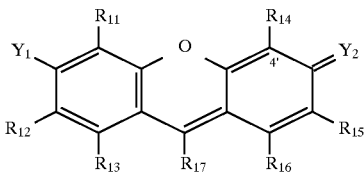

where $Y_1$ and $Y_2$ taken separately are either hydroxyl, oxygen, iminium or amine, the iminium and amine preferably being a tertiary iminium or amine. $R_{11}$–$R_{17}$ may be any substituent which is compatible with the energy transfer dyes of the present invention, it being noted that the $R_{11}$–$R_{17}$ may be widely varied in order to alter the spectral and mobility properties of the dyes.

The energy transfer dye also includes an acceptor dye which absorbs the excitation energy emitted by the donor dye and fluoresces at a second wavelength in response.

The energy transfer dye also includes a linker which attaches the donor dye to the acceptor dye, the linker having a 4' end which includes a $R_1XC(O)R_2$ group where $R_1$ is a $C_{1-5}$ alkyl attached to the 4' ring position of the donor dye, $C(O)$ is a carbonyl group, X is either NH, sulfur or oxygen, and $R_2$ includes an alkene, diene, alkyne, a five and six membered ring having at least one unsaturated bond or a fused ring structure which is attached to the carbonyl carbon.

According to this embodiment, the donor dye may optionally be a member of the class of dyes where $R_{17}$ is a phenyl or substituted phenyl. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes. Further according to this embodiment, the acceptor dye may optionally be a member of the xanthene, cyanine, phthalocyanine and squaraine classes of dyes.

In another embodiment, the energy transfer fluorescent dyes include a donor dye which is a member of the xanthene class of dyes, an acceptor dye which is a member of the xanthene, cyanine, phthalocyanine and squaraine classes of dyes which is capable of absorbing the excitation energy emitted by the donor dye and fluorescing at a second wavelength in response, and a linker attaching the donor dye to the acceptor dye. According to this embodiment, the acceptor has an emission maximum that is greater than about 600 nm or at least about 100 nm greater than the absorbance maximum of the donor dye. In one embodiment, the linker is attached to the donor dye at the 4' ring position of the xanthene ring structure. In another embodiment, the linker includes a $R_3X$ group where $R_3$ is a $C_{1-5}$ alkyl attached to the 4' ring position of the donor xanthene ring structure and X is either NH, sulfur or oxygen. In yet another embodiment, the linker includes a $R_3XC(O)R_4N$ group where $R_3$ is a $C_{1-5}$ alkyl attached to the donor dye at the 4' xanthene ring position, X is either NH, sulfur or oxygen, C(O) is a carbonyl group, and $R_4$ has a carbon backbone such that $C(O)R_4N$ forms an amino acid subunit.

In another embodiment, the energy transfer fluorescent dyes have donor and acceptor dyes with the general structure

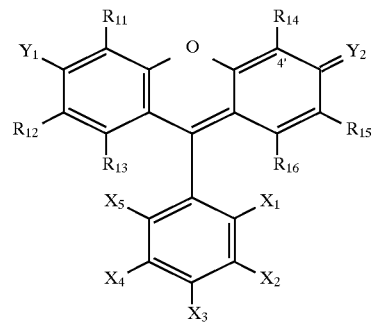

where $Y_1$ and $Y_2$ taken separately are either hydroxyl, oxygen, iminium or amine, the iminium and amine preferably being a tertiary iminium or amine and $R_{11}$–$R_{17}$ are any substituents which are compatible with the energy transfer dyes of the present invention.

According to this embodiment, the linker is the $X_3$ substituent of the donor and acceptor dyes. In this embodiment, the linker is preferably short and/or rigid as this has been found to enhance the transfer of energy between the donor and acceptor dyes.

In addition to the above-described novel energy transfer fluorescent dyes, the present invention also relates to fluorescent reagents containing the energy transfer fluorescent dyes. In general, these reagents include any molecule or material to which the energy transfer dyes of the invention can be attached and used to detect the presence of the reagent based on the fluorescence of the energy transfer dye. In one embodiment, a fluorescent reagent is provided which includes a nucleoside or a mono-, di- or triphosphate nucleotide labelled with an energy transfer fluorescent dye. The nucleotide may be a deoxynucleotide which may be used for example, in the preparation of dye labelled oligonucleotides. The nucleotide may also be a dideoxynucleoside which may be used, for example, in dye terminator sequencing. In another embodiment, the fluorescent reagent includes an oligonucleotide labelled with an energy transfer fluorescent dye. These reagents may be used, for example, in dye primer sequencing.

The present invention also relates to methods which use the energy transfer fluorescent dyes and reagents of the present invention. In one embodiment, the method includes forming a series of different sized oligonucleotides labelled with an energy transfer fluorescent dye of the present invention, separating the series of labelled oligonucleotides based on size, detecting the separated labelled oligonucleotides based on the fluorescence of the energy transfer dye.

In one embodiment of this method, a mixture of extended labelled primers is formed by hybridizing a nucleic acid sequence with an oligonucleotide primer in the presence of deoxynucleotide triphosphates, and at least one dye labelled dideoxynucleotide triphosphate and a DNA polymerase. The DNA polymerase serves to extend the primer with the deoxynucleotide triphosphates until a dideoxynucleotide triphosphate is incorporated which terminates extension of the primer. Once terminated, the mixture of extended primers are separated and detected based on the fluorescence of the dye on the dideoxynucleoside. In a variation of this embodiment, four different fluorescently labelled dideoxynucleotide triphosphates are used, i.e., a fluorescently labelled dideoxycytosine triphosphate, a fluorescently labelled dideoxyadenosine triphosphate, a fluorescently labelled dideoxyguanosine triphosphate, and a fluorescently labelled dideoxythymidine triphosphate. In an alternate embodiment of this method, the oligonucleotide primer is fluorescently labelled as opposed to the deoxynucleotide triphosphate.

The present invention also relates to kits containing the dyes and reagents for performing DNA sequencing using the dyes and reagents of present invention.

DETAILED DESCRIPTION

Figure 1:
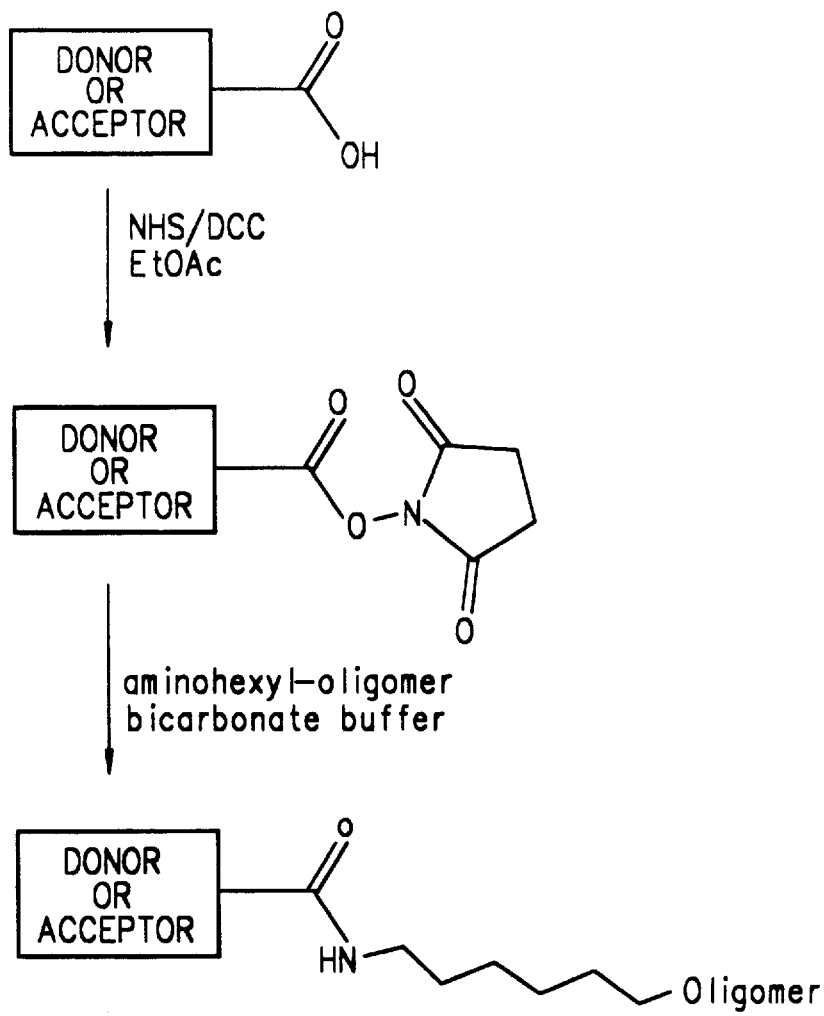
FIG. 1 illustrates the modification of a carboxy substituent on a energy transfer dye to an activated N-hydroxysuccinimidyl (NHS) ester which is then reacted with an aminohexyl-oligomer to form a dye labelled oligonucleotide primer.

The present invention relates to novel energy transfer fluorescent dyes which exhibit enhanced fluorescence intensity. The present invention also relates to reagents which include the energy transfer dyes of the present invention, methods for using the dyes and reagents, and kits within which the dyes and reagents are included.

I. Energy Transfer Dyes Of The Present Invention

In general, the energy transfer dyes of the present invention include a donor dye which absorbs light at a first wavelength and emits excitation energy in response, an acceptor dye which is capable of absorbing the excitation energy emitted by the donor dye and fluorescing at a second wavelength in response, and a linker which attaches the donor dye to the acceptor dye. With regard to all of the molecular structures provided herein, it is intended that these molecular structures encompass not only the exact electronic structure presented, but also include all resonant structures and protonation states thereof.

One class of energy transfer fluorescent dyes according to the present invention includes a donor dye which is a member of the xanthene class of dyes. As used herein, xanthene dyes include all molecules having the general structure

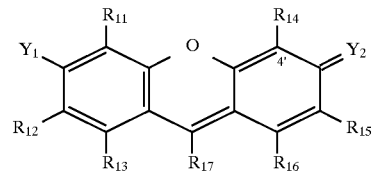

where $Y_1$ and $Y_2$ taken separately are either hydroxyl, oxygen, iminium or amine, the iminium and amine preferably being a tertiary iminium or amine. When $Y_1$ is hydroxyl and $Y_2$ is oxygen, and $R_{17}$ is a phenyl or substituted phenyl, the dye is a member of the fluorescein class of dyes. When $Y_1$ is amine and $Y_2$ is iminium, and $R_{17}$ is a phenyl or substituted phenyl, the dye is a member of the rhodamine class of dyes.

$R_{11}$–$R_{17}$ may be any substituent which is compatible with the energy transfer dyes of the present invention, it being noted that the $R_{11}$–$R_{17}$ may be widely varied in order to alter the spectral and mobility properties of the dyes. The number indicated in the ring structure indicates the 4' position on the xanthene ring structure. For the energy transfer dyes of the present invention in which the linker is attached to the 4' position of the xanthene ring structure, the $R_{14}$ substituent corresponds to the linker.

Examples of $R_{11}$–$R_{17}$ substituents include, but not limited to hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof.

In one embodiment, $R_{15}$ and $R_{16}$ are taken together to form a substituted or unsubstituted benzene ring. This class of xanthene dyes are referred to herein as asymmetric benzoxanthene dyes and are described in U.S. application Ser. No. 08/626,085, filed Apr. 1, 1996, entitled Asymmetric Benzoxanthene Dyes, by Scott C. Benson, et al. which is incorporated herein by reference.

In another embodiment, $R_{17}$ is a phenyl or substituted phenyl having the general formula

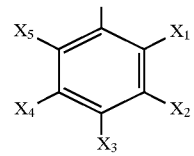

Substituents $X_1$–$X_5$ on the phenyl ring can include hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof.

As used here, alkyl denotes straight-chain and branched hydrocarbon moieties, i.e., methyl, ethyl, propyl, isopropyl, tert-butyl, isobutyl, sec-butyl, neopentyl, tert-pentyl, and the like. Substituted alkyl denotes an alkyl moiety substituted with any one of a variety of substituents, including, but not limited to hydroxy, amino, thio, cyano, nitro, sulfo, and the like. Haloalkyl denotes a substituted alkyl with one or more halogen atom substituents, usually fluoro, chloro, bromo, or iodo. Alkene denotes a hydocarbon wherein one or more of the carbon-carbon bonds are double bonds, and the non-double bonded carbons are alkyl or substituted alkyl. Alkyne denotes a hydrocarbon where one or more of the carbons are bonded with a triple bond and where the non-triple bonded carbons are alkyl or substituted alkyl moieties. Sulfonate refers to moieties including a sulfur atom bonded to 3 oxygen atoms, including mono- and di-salts thereof, e.g., sodium sulfonate, potassium sulfonate, disodium sulfonate, and the like. Amino refers to moieties including a nitrogen atom bonded to 2 hydrogen atoms, alkyl moieties, or any combination thereof. Amido refers to moieties including a carbon atom double bonded to an oxygen atom and single bonded to an amino moiety. Nitrile refers to moieties including a carbon atom triple bonded to a nitrogen atom. Alkoxy refers to a moiety including an alkyl moiety single bonded to an oxygen atom. Aryl refers to single or multiple phenyl or substituted phenyl, e.g., benzene, naphthalene, anthracene, biphenyl, and the like.

$R_{11}-R_{17}$ may also each independently be a linking moiety which may be used to attach the energy transfer dye to a reagent, such as a nucleotide, nucleoside or oligonucleotide. Examples of linking moieties include isothiocyanate, sulfonyl chloride, 4,6-dichlorotriazinylamine, succinimidyl ester, or other active carboxylate whenever the complementary functionality is amine. Preferably the linking group is maleimide, halo acetyl, or iodoacetamide whenever the complementary functionality is sulfhydryl. See R. Haugland, *Molecular Probes Handbook of Fluorescent Probes and Research Chemicals*, Molecular probes, Inc. (1992). In a particularly preferred embodiment, as illustrated in FIG. 1, the linking group is an activated NHS ester formed from a carboxyl group on either the donor or acceptor dye which can be reacted with an aminohexyl-oligomer to form a dye labelled oligonucleotide primer.

The energy transfer fluorescent dyes of this embodiment also include an acceptor dye which is capable of absorbing the excitation energy emitted by the donor dye and fluorescing at a second wavelength in response, and a linker which attaches the donor dye to the acceptor dye. As illustrated below, the linker has a 4' end which includes a $R_1XC(O)R_2$ group where $R_1$ is a $C_{1-5}$ alkyl which is attached to the 4' ring position of the donor xanthene dye, X is either NH, sulfur or oxygen, C(O) is a carbonyl group, and $R_2$ includes an alkene, diene, alkyne, a five and six membered ring having at least one unsaturated bond or a fused ring structure which is attached to the carbonyl carbon. Examples of five or six membered ring include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

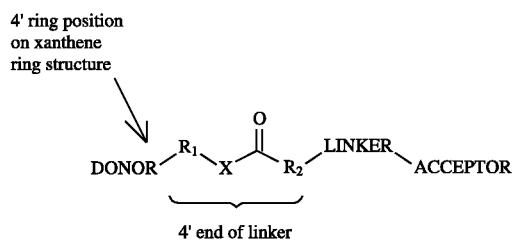

This class of energy transfer dyes exhibit enhanced fluorescent strength as compared to the acceptor fluorophore itself and energy transfer fluorescent dyes having the same donor-acceptor pair where the linkage between the donor-acceptor pair is different.

The present invention also relates to a second class of energy transfer fluorescent dyes in which the donor dye is a member of the xanthene class of dyes and the acceptor dye is a member of the xanthene, cyanine, phthalocyanine and squaraine classes of dyes. The donor is preferably a member of the fluorescein class of dyes and the acceptor preferably has an emission maximum that is greater than about 600 nm and/or preferably has an emission maximum that is at least about 100 nm greater than the absorbance maximum of the donor dye.

The second class of energy transfer dyes of the present invention exhibit unusually large Stoke shifts, as measured by the difference between the absorbance of the donor and the emission of the acceptor. In addition, these dyes exhibit efficient energy transfer in that minimal donor fluorescence is observed.

This class of energy transfer dyes also includes a linker which attaches the donor dye to the acceptor dye. In one embodiment, the linker is attached to the 4' position of the donor dye's xanthene ring structure and preferably includes a $R_3X$ group where $R_3$ is a $C_{1-5}$ alkyl attached to the 4' ring position and X is either NH, sulfur or oxygen. In cases where the acceptor dye is a member of the xanthene class of dyes, the linker is preferably attached to acceptor at the 5 position of the xanthene ring structure.

The present invention also relates to a third class of energy transfer fluorescent dyes in which the donor and acceptor dyes each have the general structure

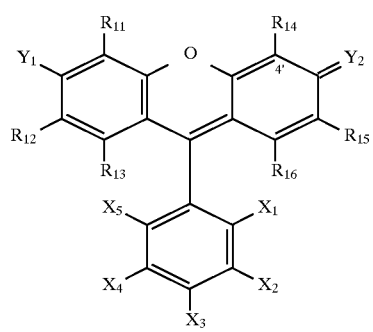

where $Y_1$, $Y_2$, $R_{11}-R_{16}$ and $X1-X_5$ are as specified above.

According to this embodiment, the $X_3$ substituent for both the donor and acceptor dyes correspond to a linker which attaches the two dyes. In this embodiment, the linker attaching the donor to the acceptor dye is preferably short and/or rigid as this has been found to enhance the transfer of energy between the donor and acceptor dyes.

Described herein in greater detail are three classes of energy transfer dyes of the present invention.

TABLE 1
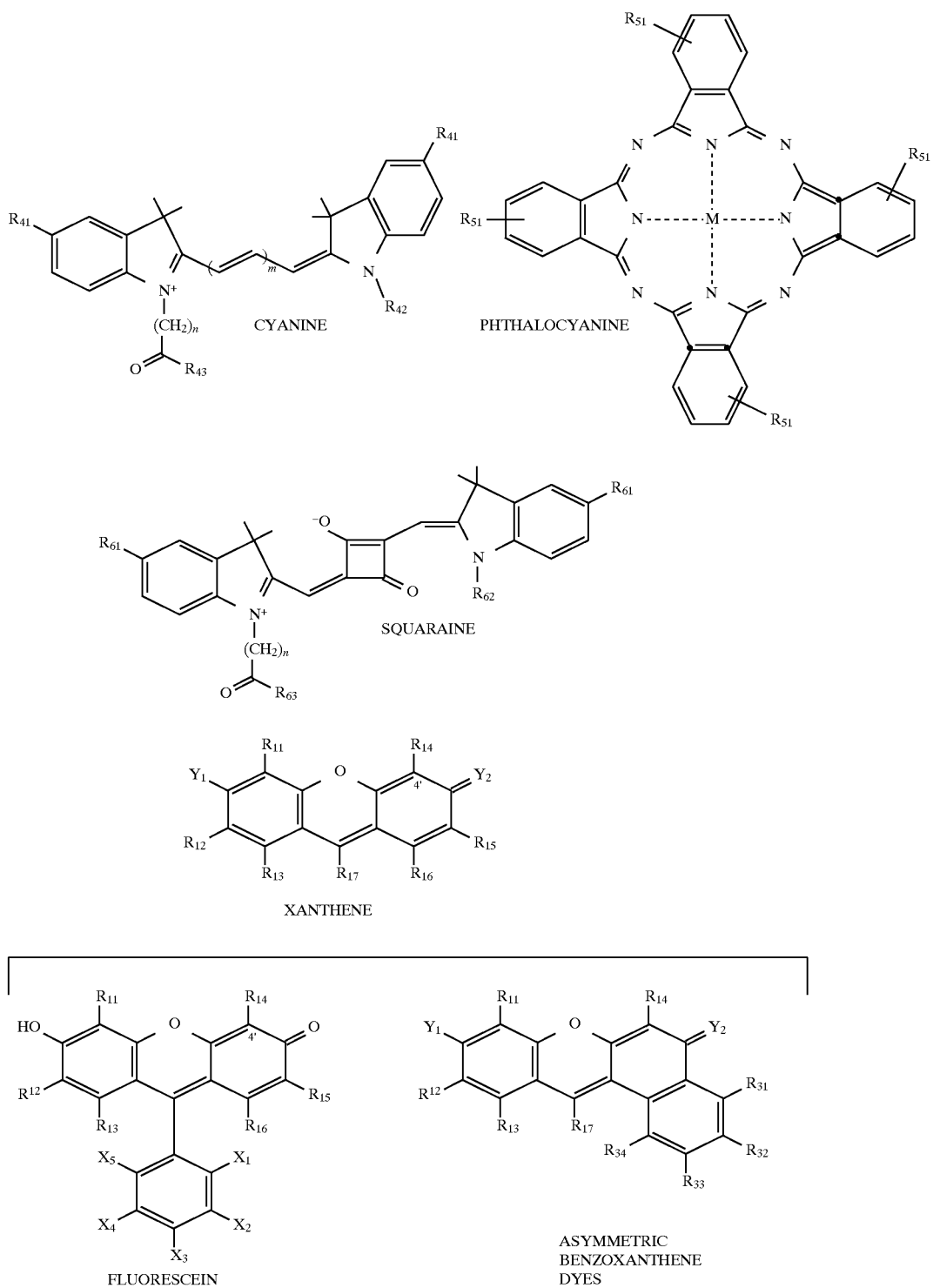

TABLE 1-continued

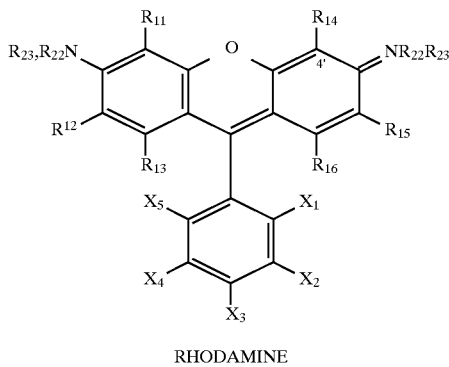

RHODAMINE

A. First Class Of Energy Transfer Dyes

As described above, the first class of energy transfer dyes according to the present invention includes a donor dye which is a member of the xanthene class of dyes and hence has a xanthene ring structure with a 4' ring position. Within this class of dyes, the acceptor dye is a dye which is capable of absorbing the excitation energy emitted by the donor dye and fluorescing at a second wavelength in response.

According to this embodiment, the donor may be a member of the fluorescein, rhodamine or asymmetric benzoxanthene classes of dyes, these dyes each being members of the broader xanthene class of dyes.

Examples of classes of acceptor dyes which may be used in the energy transfer fluorescent dye of this embodiment include, but are not limited to, xanthene dyes, cyanine dyes, phthalocyanine and squaraine dyes. Also illustrated in Table 1 are the general ring structures for these dyes.

Illustrated in Table 1 are the general structural formulas for the xanthene (including fluorescein, rhodamine and asymmetric benzoxanthene dyes), cyanine, phthalocyanine and squaraine classes of dyes. The substituents illustrated on these dyes, $Y_1$, $Y_2$, $R_{11}$–$R_{17}$, $R_{22}$, $R_{23}$, $R_{31}$–$R_{34}$, $R_{41}$–$R_{43}$, $R_{51}$, $R_{61}$–$R_{63}$, and $X_1$–$X_5$, may be selected from wide variety of substituents which may be incorporated onto these different classes of dyes since all dyes having the general xanthene, fluorescein, rhodamine, asymmetric benzoxanthene, cyanine, phthalocyanine and squaraine ring structures are intended to fall within the scope of this invention.

Examples of donor dyes which may be used in this embodiment include, but are not limited to fluorescein, 5-carboxyfluorescein, 5-carboxy-HEX, NAN, Cl-FLAN, TET, JOE, ZOE, rhodamine, 5-carboxyrhodamine, 3-carboxy R110, 5-carboxy R6G, 4,7-dichlorofluoresceins (See U.S. Pat. No. 5,188,934), asymmetric benzoxanthene dyes (See U.S. application Ser. No. 08/626,085, filed Apr. 1, 1996), and N,N,N',N'-tetramethyl 5-carboxyrhodamine (TAMRA).

Examples of acceptor dyes which may be used in this embodiment include, but are not limited to 5-carboxyfluorescein, 4,7-dichlorofluoresceins, asymmetric benzoxanthene dyes, 5-carboxy-HEX, NAN, Cl-FLAN, TET, JOE, ZOE, rhodamine, 5-carboxyrhodamine, 3-carboxy R110, 5-carboxy R6G, N,N,N',N'-tetramethyl 5-carboxyrhodamine (TAMRA), 5-carboxy-X-rhodamine (ROX) and Cy5. Illustrated in Table 2 are the structures of these dyes.

In the first class of energy transfer dyes according to the present invention, the linker includes a 4' end which is attached to the donor dye at the 4' position of the xanthene ring structure. The 4' end of the linker includes a $R_1XC(O)R_2$ group where $R_1$ is a $C_{1-5}$ alkyl attached to the 4' ring position of the donor xanthene dye, X is either NH, sulfur or oxygen, C(O) is a carbonyl group, and $R_2$ includes a an alkene, diene, alkyne, a five and six membered ring having at least one unsaturated bond or a fused ring structure which is attached to the carbonyl carbon. Examples of five or six membered ring include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene. Table 3 illustrates examples of $C(O)R_2$ groups which may be used in the first class of dyes.

TABLE 2
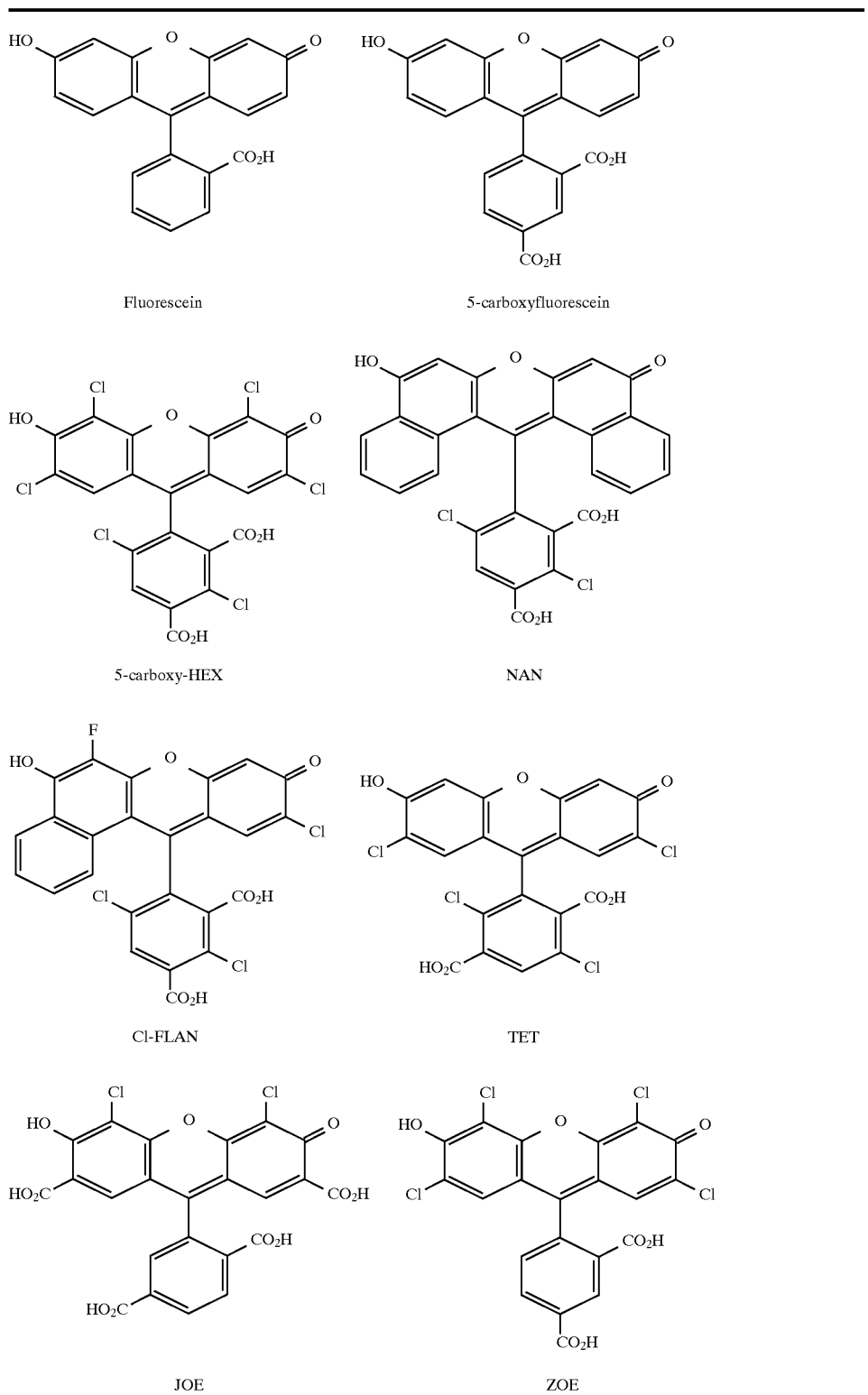

TABLE 2-continued
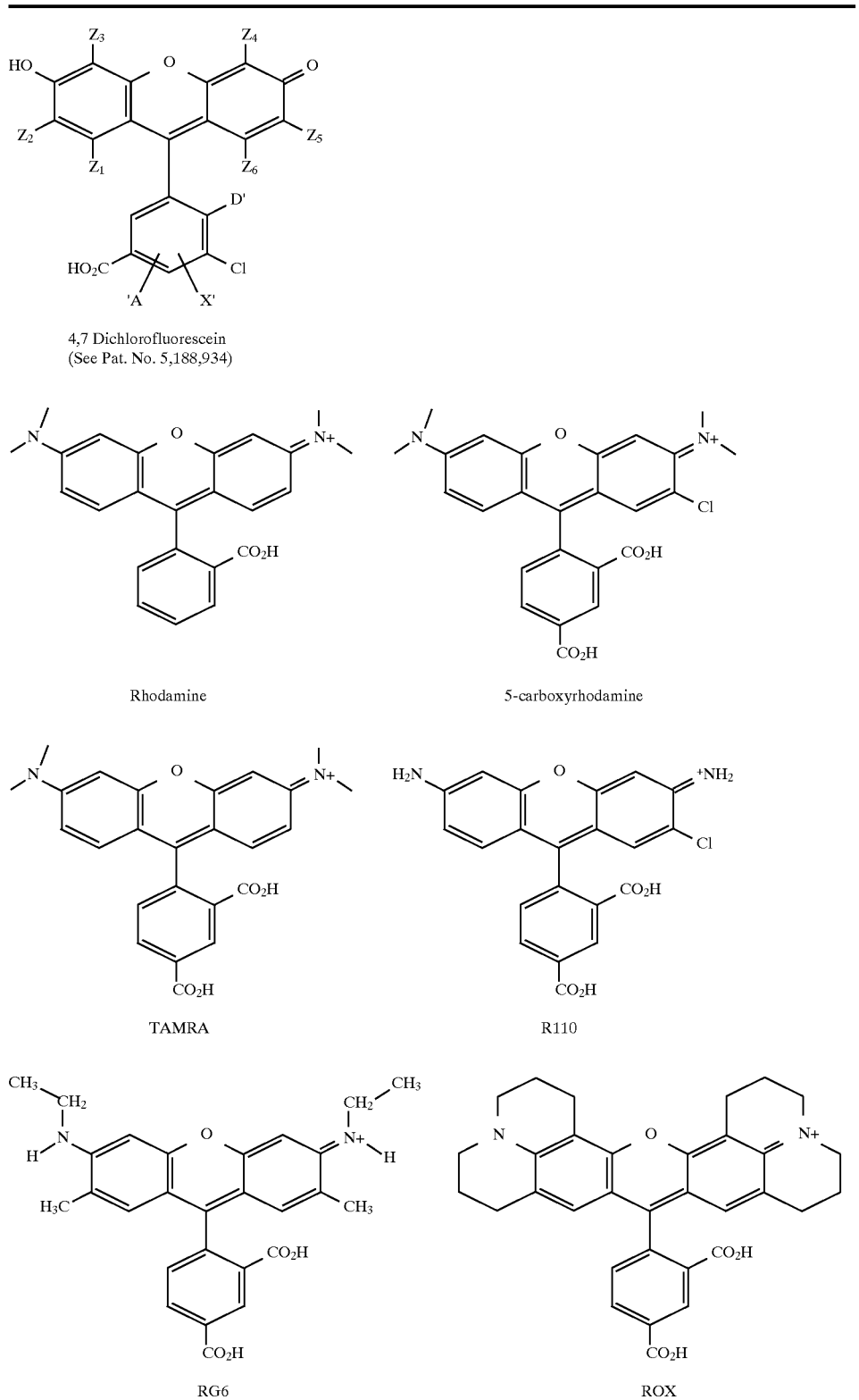
4,7 Dichlorofluorescein
(See Pat. No. 5,188,934)
Rhodamine
5-carboxyrhodamine
TAMRA
R110
RG6
ROX TABLE 2-continued
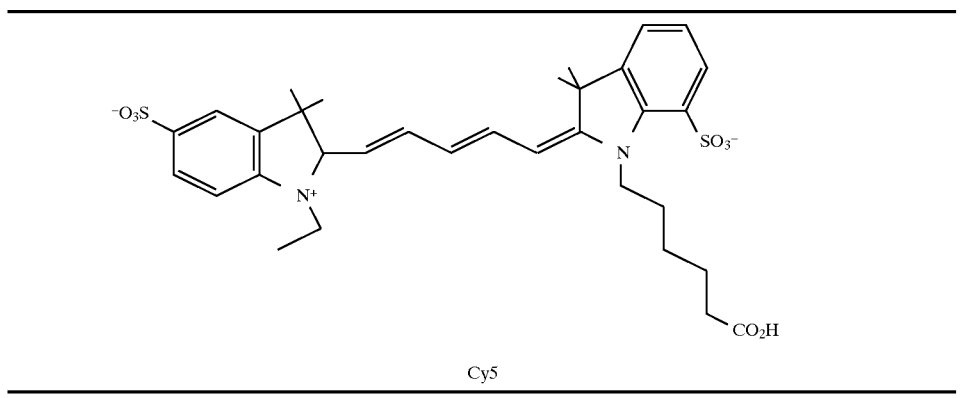
Cy5
| TABLE 3 | TABLE 3-continued |
|---|---|
| 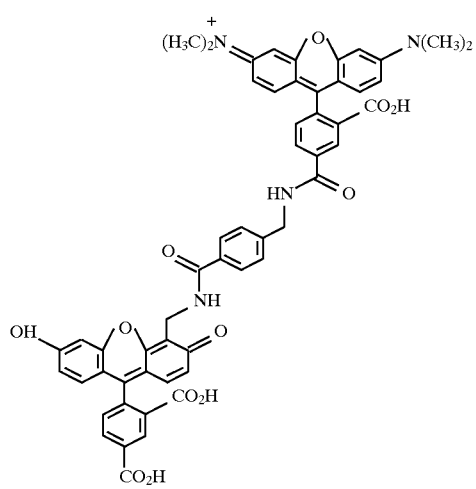<br>5TMR-B-CF | 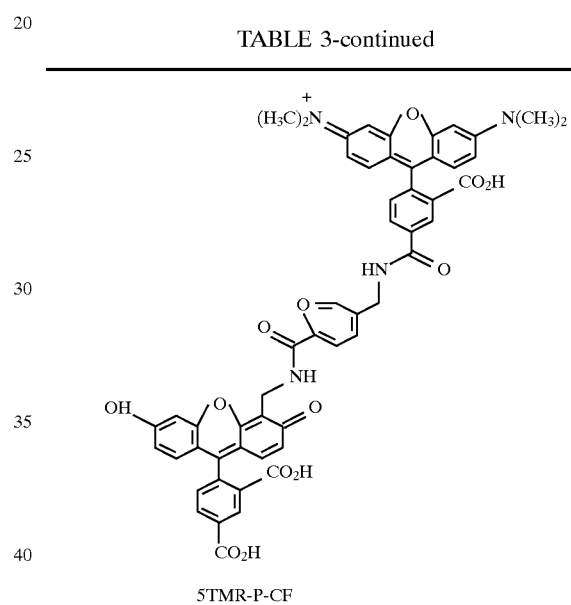<br>5TMR-P-CF |
| 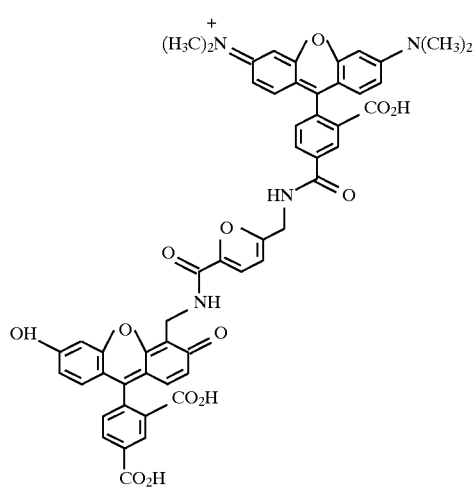<br>5TMR-F-CF | 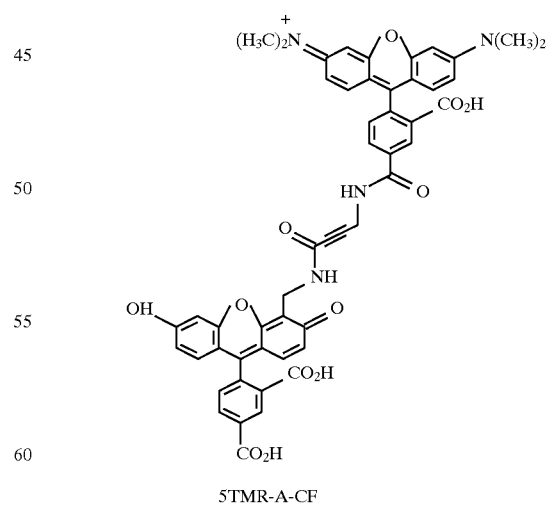<br>5TMR-A-CF |

TABLE 3-continued

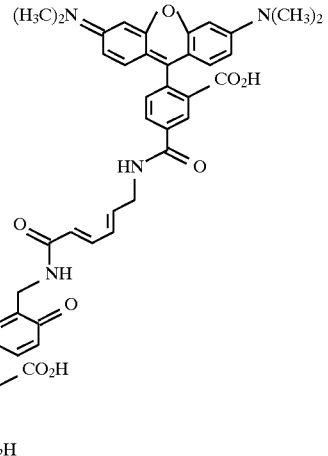

5TMR-D-CF

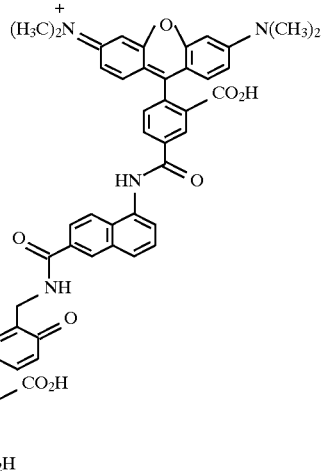

5TMR-N-CF

Figure 2:
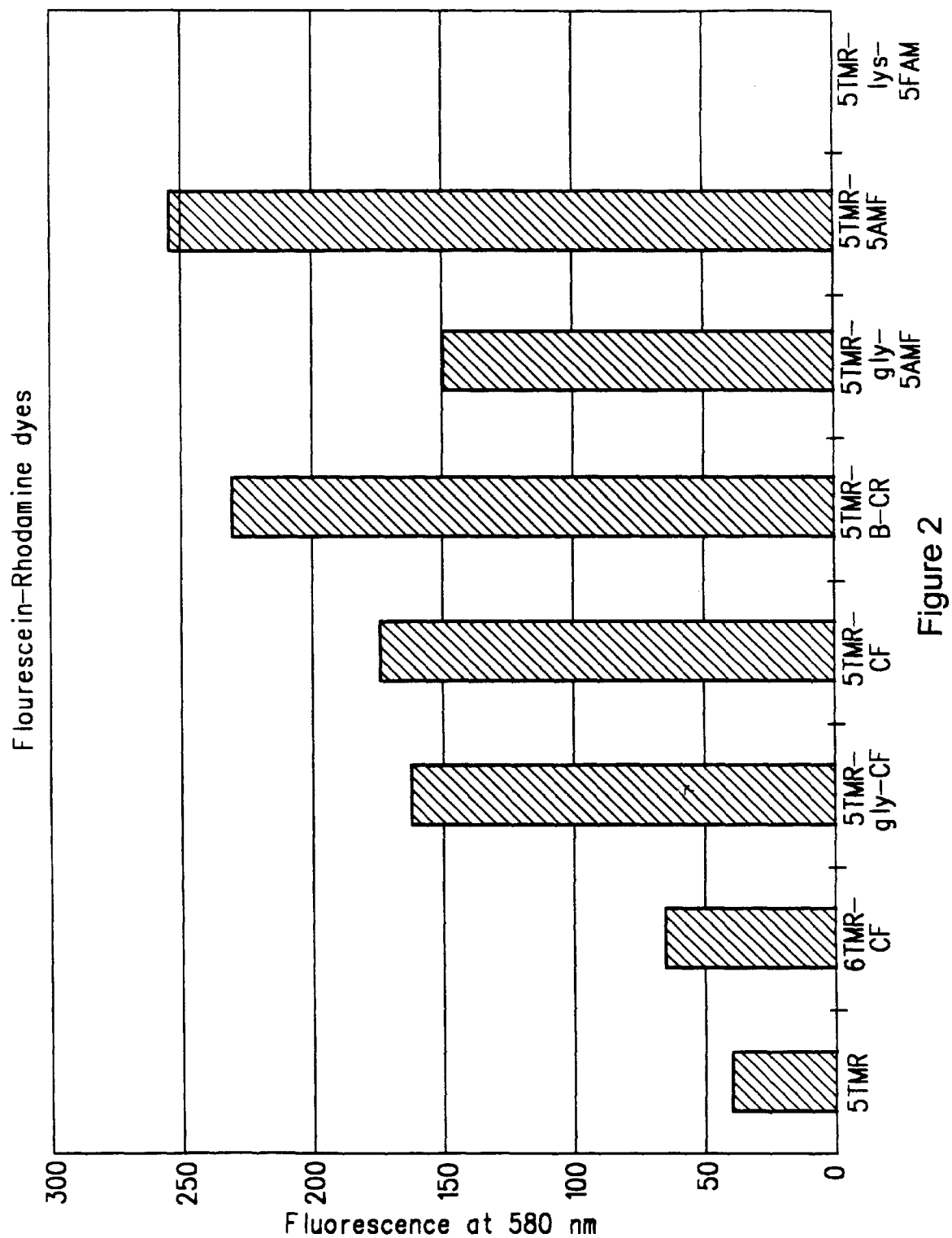
FIG. 2 compares the fluorescence emission strength of a series of energy transfer dyes of the present invention to other energy transfer dyes and the acceptor dye alone.

As illustrated in Example 4 and FIG. 2, energy transfer dyes such as 5-TMR-B-CF, which include a donor, acceptor and linker as specified above exhibit enhanced fluorescence as compared to the acceptor itself and energy transfer fluorescent dyes having the same donor-acceptor pair where the linker between the donor-acceptor pair is different. Without being bound by theory, the enhanced fluorescence intensity observed is believed to be due to an improved energy transfer orientation between the donor and acceptor dye which is achieved and maintained by the relatively rigid $R_2$ portion of the linker. As a result, the energy transfer fluorescent dyes of the present invention exhibit enhanced fluorescent strength as compared to the acceptor fluorophore itself and energy transfer fluorescent dyes having the same donor-acceptor pair where the linkage between the donor-acceptor pair is different. The enhanced fluorescent strength of these dyes is particularly evident in the presence of 8M urea which serves to reduce dye stacking.

In one variation of this embodiment, as illustrated below, the 4' end of the linker includes a $R_1XC(O)R_2N$ group where $R_1$ is a $C_{1-5}$ alkyl attached to the 4' ring position of the donor xanthene dye, X is either NH, sulfur or oxygen, C(O) is a carbonyl group, and $R_2$ has a carbon backbone such that $C(O)R_2N$ forms an amino acid subunit, the carbonyl carbon being attached to X to form either an amide, ester or thioester linkage.

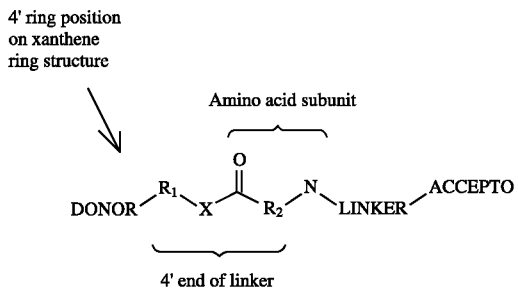

In another variation of this embodiment, the acceptor is a member of the xanthene class of dyes having the general structure

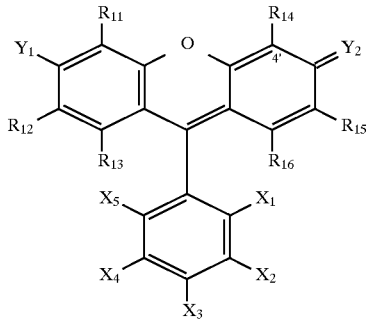

where $Y_1$, $Y_2$, $R_{11}$–$R_{16}$ and $X_1$–$X_5$ are as specified above.

According to this variation, it is preferred that the $X_3$ substituent of the acceptor xanthene dye include the linker and the donor dye attached thereto, as illustrated below.

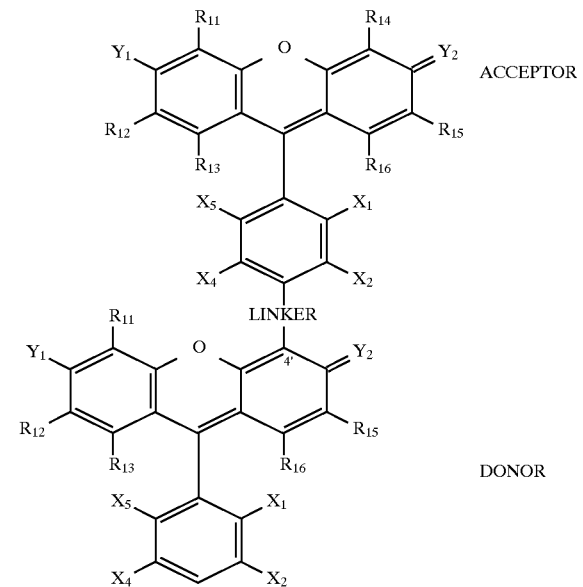

According to this variation, the end of the linker attached to the acceptor preferably includes a carbonyl group which forms part of an ester, ketone, amide or thioester functional group, the linker being attached to the acceptor by the carbon of the carbonyl group.

Table 4 provides examples of the above-described energy transfer dyes according to this embodiment of the invention.

It is noted that although the dyes illustrated in Table 4 include a 5-carboxyfluorescein donor dye and a TAMRA acceptor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.

TABLE 4

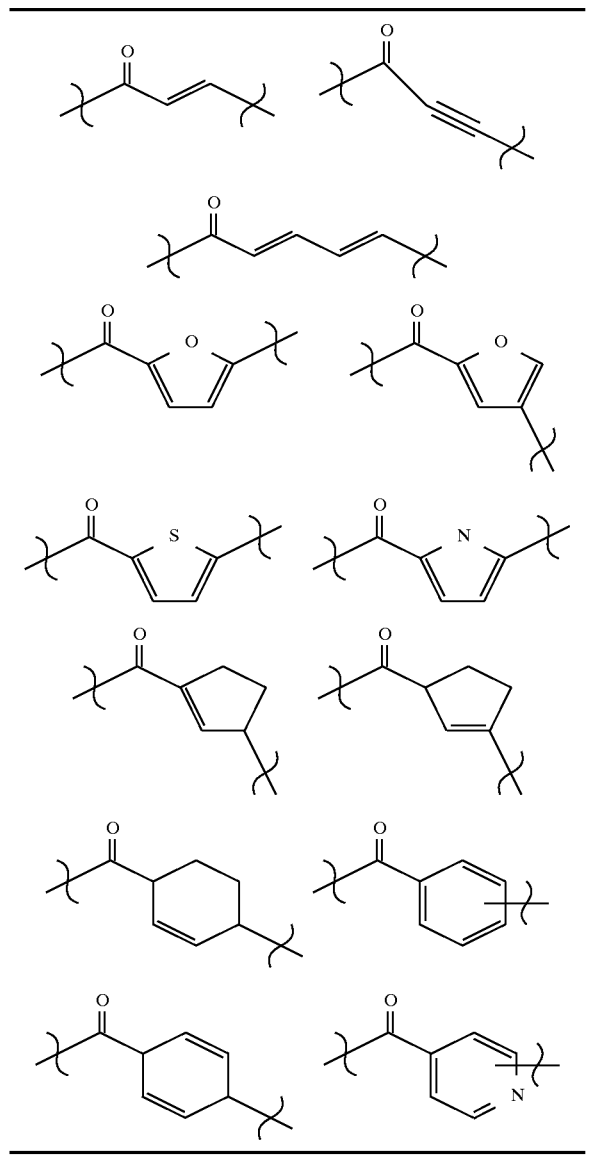

B. Second Class Of Energy Transfer Dyes

The present invention also relates to a second class of energy transfer fluorescent dyes in which the donor dye is a member of the xanthene class of dyes, and the acceptor dye is a member of the xanthene, cyanine, phthalocyanine or squaraine classes of dyes. Within this class of energy transfer dyes, it is preferred that the donor be a member of the fluorescein class of dyes and the acceptor dye have an emission maximum that is greater than about 600 nm and/or an emission maximum that is at least about 100 nm greater than the absorbance maximum of the donor dye.

The second class of dyes of the present invention exhibit unusually large Stoke shifts, as measured by the difference between the absorbance of the donor and the emission of the acceptor. In addition, these dyes exhibit efficient energy transfer in that minimal donor fluorescence is observed.

Examples of acceptor dyes which may be used in this embodiment include, but are not limited to 5-carboxy-X-rhodamine (ROX) and Cy5.

The energy transfer dyes of this embodiment also include a linker which attaches the donor to the acceptor. In one variation of this embodiment, as illustrated below, the linker is attached to the donor dye at the 4' position of the xanthene ring structure. According to this embodiment, the 4' end of the linker may include a $R_3X$ group where $R_3$ is a $C_{1-5}$ alkyl attached to the 4' ring position and X is either NH, sulfur or oxygen.

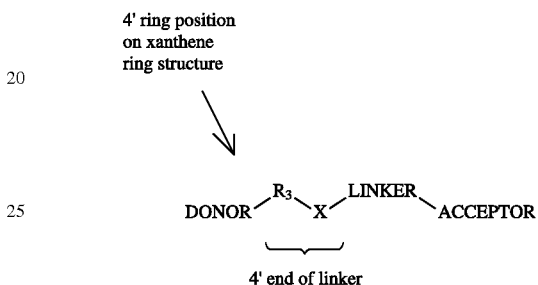

Alternatively, as illustrated below, the 4' end of the linker may include a $R_3XC(O)R_4N$ group where $R_3$ is a $C_{1-5}$ alkyl attached to the donor dye at the 4' position of the xanthene ring structure, X is either NH, sulfur or oxygen, C(O) is a carbonyl group, and $R_4$ has a carbon backbone such that $C(O)R_4N$ forms an amino acid subunit. $R_4$ may be selected such that the amino acid subunit formed by $C(O)R_4N$ corresponds to one of the 20 naturally occurring amino acids. Alternatively, $R_4$ may be selected such that the amino acid subunit formed by $C(O)R_4N$ does not correspond to any of the 20 naturally occurring amino acids.

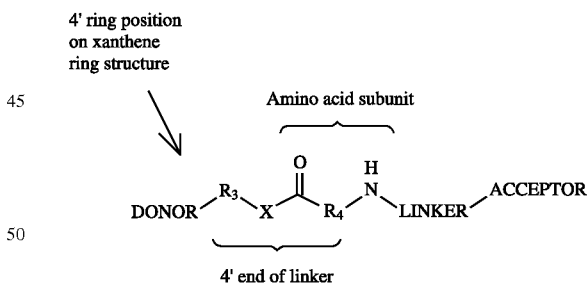

In another variation of this embodiment, $R_4$ includes an alkene, diene, alkyne, a five and six membered ring having at least one unsaturated bond or a fused ring structure which is attached to the carbonyl carbon. Examples of five or six membered ring include, but are not limited to cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine and oxazine. Examples of fused ring structures include, but are not limited to indene, benzofuran, thionaphthene, indole and naphthalene.

In a variation of this embodiment, the acceptor is a member of the xanthene class of dyes having the general structure

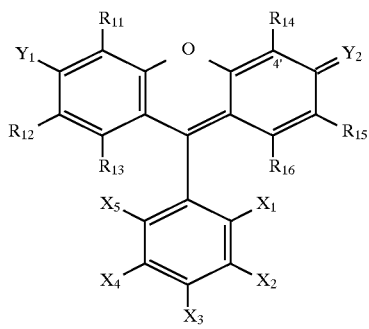

where $Y_1$, $Y_2$, $R_{11}$–$R_{16}$ and $X_1$–$X_5$ are as specified above.

According to this variation, it is preferred that the $X_3$ substituent of the acceptor xanthene dye include the linker and the donor dye attached thereto, as illustrated below. Further according to this variation, the end of the linker attached to the acceptor preferably includes a carbonyl group which forms part of an ester, ketone, amide or thioester functional group, the linker being attached to the acceptor by the carbon of the carbonyl group.

Table 5 provides examples of the above-described energy transfer dyes according to the present invention. It is noted that although the dyes illustrated in Table 5 include a 5-carboxyfluorescein donor dye it should be understood that a wide variety of other xanthene dyes can be readily substituted as the donor dye. It should also be understood that a wide variety of other xanthene dyes, as well as cyanine, phthalocyanine and squaraine dyes can be readily substituted for the 5-carboxy ROX and Cy5 acceptor dyes, as has been described above, all of these variations with regard to the donor and acceptor dyes falling within the scope of the invention.

Figure 3:
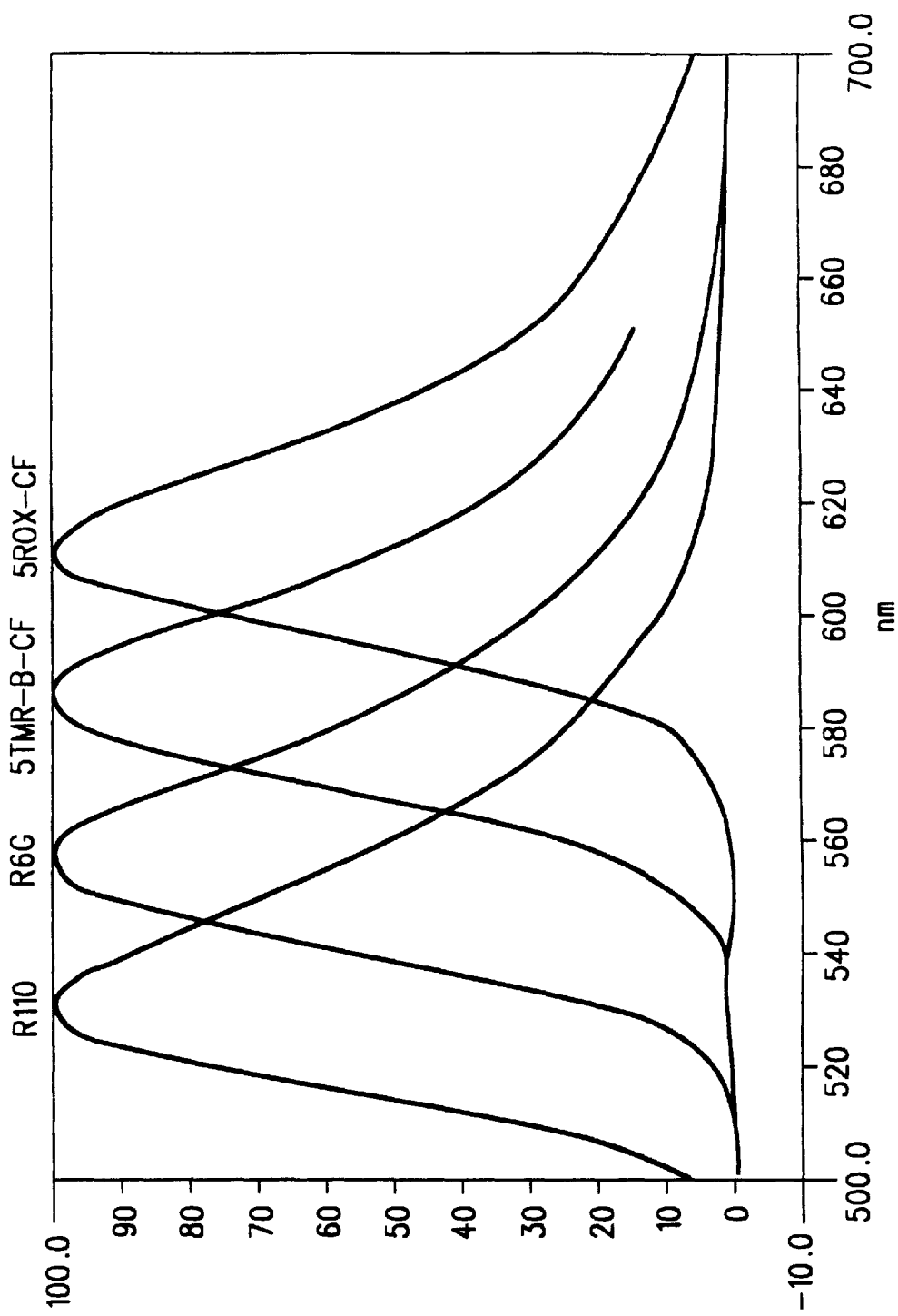
FIG. 3 illustrates a set of four dyes (3-carboxy-R110, 5-carboxy-R6G, 5TMR-B-CF and 5ROX-CF) which are spectrally resolvable from each other.
Figure 4:
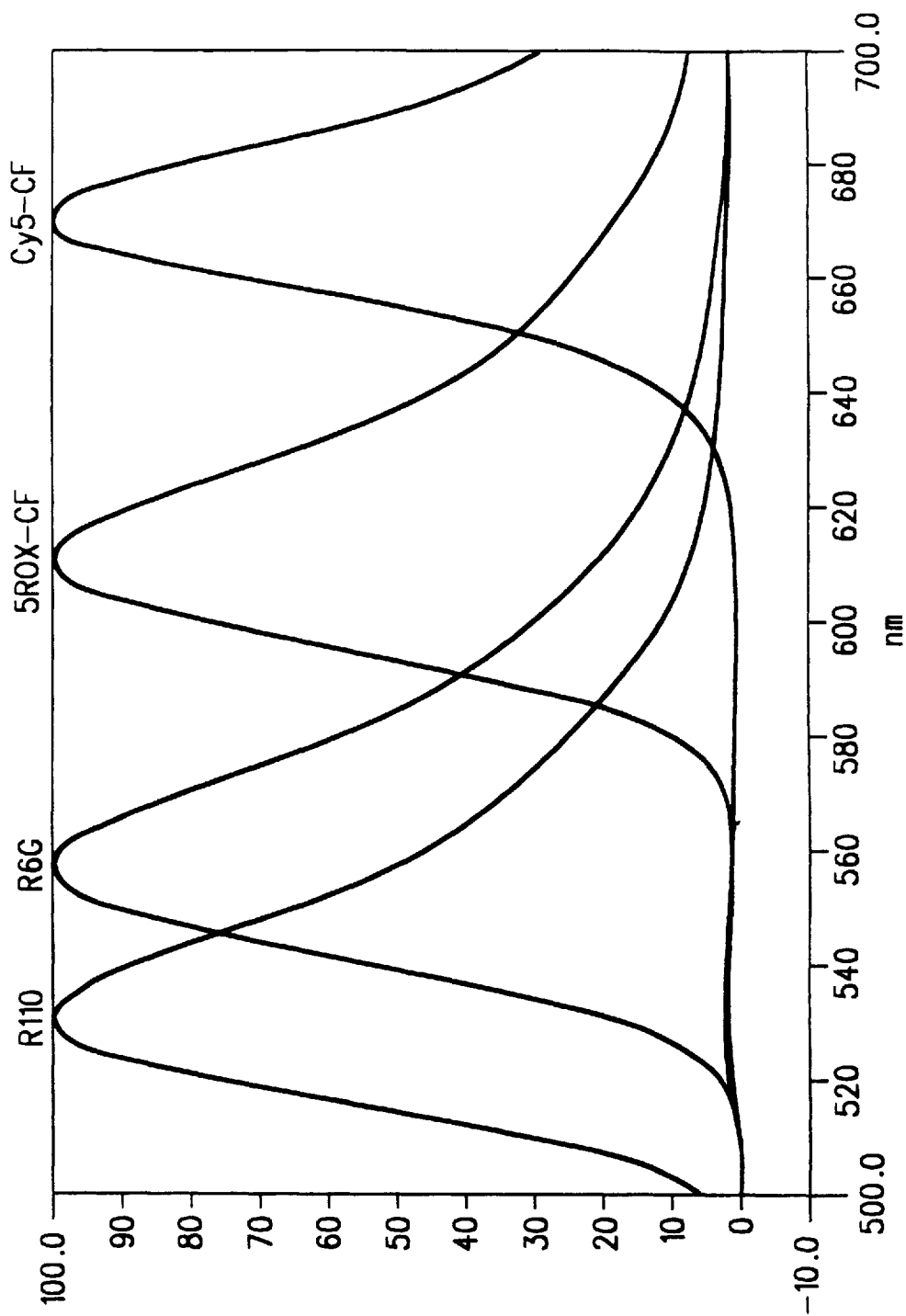
FIG. 4 illustrates a set of four dyes (3-carboxy-R110, 5-carboxy-R6G, 5ROX-CF and Cy5-CF) which are spectrally resolvable from each other.

The energy transfer dyes of this embodiment exhibit unusually large Stoke shifts which make these dyes particularly well suited for use with dyes having smaller Stoke shifts in four dye DNA sequencing. For example, FIGS. 3 and 4 illustrate two sets of four dyes which are spectrally resolvable from each other. Within FIG. 3, 5ROX-CF is a dye falling within the scope of the second class of dyes described above. Meanwhile, FIG. 4 includes 5ROX-CF and Cy5-CF which both fall within the scope of the second class of dyes described above.

As can be seen from the emission spectra of 5ROX-CF and Cy5-CF illustrated in FIG. 4, very little fluorescence from the donor dye (5-carboxyfluorescein, 520 nm) is observed in these dyes. This is an unexpected result in view of the large difference between the emission maximum of the donor dye (fluorescein) and the absorbance maximum of the acceptor dyes (ROX, 590 nm, Cy5, 640 nm).

TABLE 5

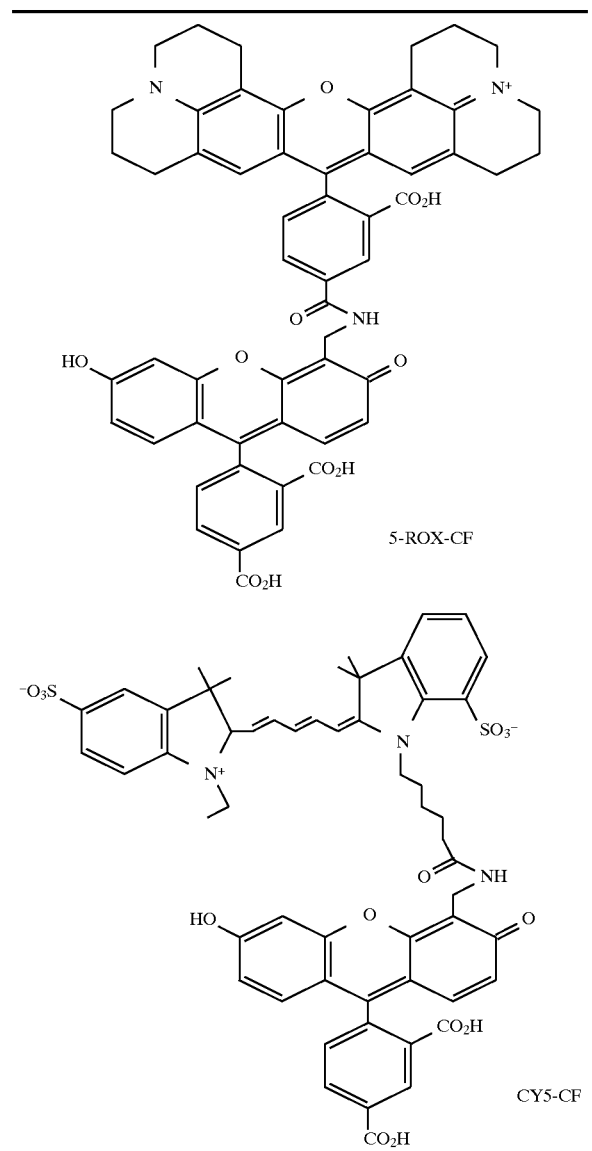

C. Third Class Of Energy Transfer Dyes

The present invention also relates to a third class of energy transfer fluorescent dyes, illustrated below, in which the donor dye and acceptor each are members of the xanthene class of dyes having the general structure

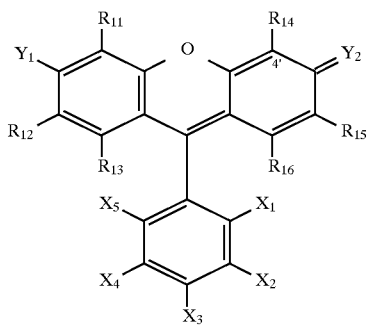

where $Y_1$, $Y_2$, $R_{11}$–$R_{16}$ and $X_1$–$X_5$ are as specified above.

According to this embodiment, the $X_3$ substituent for both the donor and acceptor dyes corresponds to a linker which attaches the two dyes, as illustrated below.

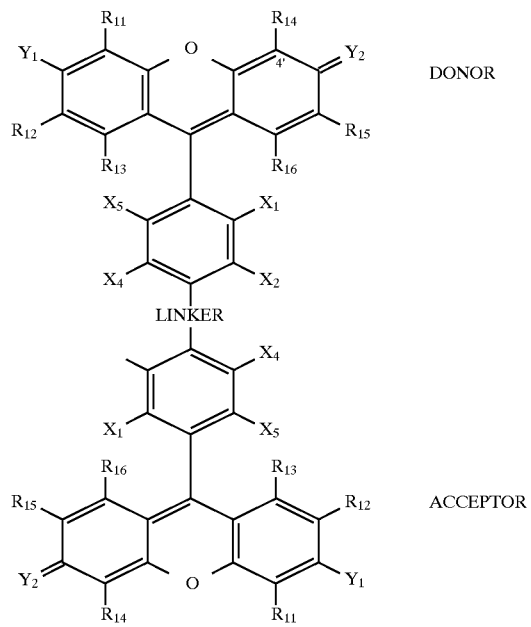

In this embodiment, the linker is preferably short and/or rigid as this has been found to enhance the transfer of energy between the donor and acceptor dyes. For example, in one variation of this embodiment, the linker preferably has a backbone attaching the donor to the acceptor which is less than 9 atoms in length. In another variation of this embodiment, the linker includes a functional group which gives the linker some degree of structural rigidity, such as an alkene, diene, an alkyne, a five and six membered ring having at least one unsaturated bond or a fused ring structure. In yet another variation, the linker has the general formula —$R_5XC(O)R_6XC(O)$— or —$R_7XC(O)$— where $R_5$, $R_6$ and $R_7$ are each selected from the group of $C_{1-4}$ alkyl, C(O) is a carbonyl group, and each X is either NH, O or S.

Examples of donor dyes which may be used in this embodiment include, but are not limited to fluorescein, 5-carboxyfluorescein, 5-carboxy-HEX, NAN, Cl-FLAN, TET, JOE, ZOE, 4,7-dichlorofluoresceins, asymmetric benzoxanthene dyes, rhodamine, 5-carboxyrhodamine, 5-carboxy-$R_{110}$, 5-carboxy-R6G and N,N,N',N'-tetramethyl 5-carboxyrhodamine (TAMRA), and 5-carboxy-X-rhodamine (ROX). Illustrated in Table 2 are the structures of these dyes.

In another variation of this embodiment, the linker includes a $R_5XC(O)$ group where $R_5$ is a $C_{1-5}$ alkyl attached to the donor dye, C(O) is a carbonyl group, and X is either NH, sulfur or oxygen. In yet another variation, the end of the linker attached to the acceptor includes a carbonyl group which forms part of an ester, ketone, amide or thioester functional group, the linker being attached to the acceptor by the carbon of the carbonyl group.

Table 6 provides examples of the third class of energy transfer dyes according to the present invention. It is noted that although the dyes illustrated in Table 6 include a 5-aminomethylfluorescein donor dye, it should be understood that a wide variety of other xanthene dyes can be readily substituted as the donor dye. It should also be understood that a wide variety of other xanthene dyes, as well as cyanine, phthalocyanine and squaraine dyes can be readily substituted for the TAMRA acceptor dye, as has been described above, all of these variations with regard to the donor and acceptor dyes falling within the scope of the invention.

TABLE 6

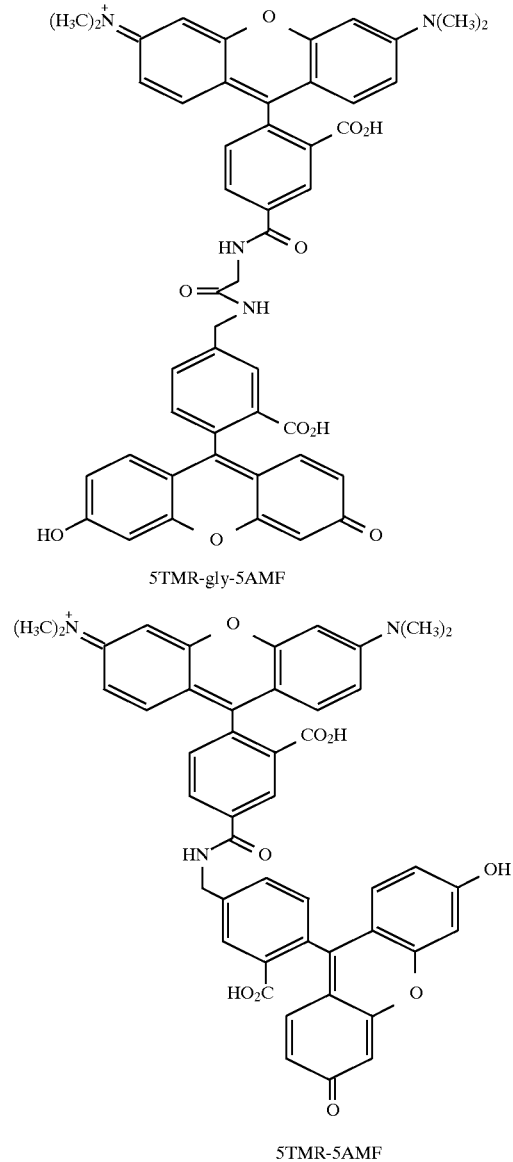

II. Reagents Including Energy Transfer Dyes Of The Present Invention

The present invention also relates to fluorescent reagents which incorporate an energy transfer fluorescent dye according to the present invention. As described in greater detail in Section III, these reagents may be used in a wide variety of methods for detecting the presence of a component in a sample.

The fluorescent reagents of the present invention include any molecule or material to which the energy transfer dyes of the invention can be attached and used to detect the presence of the reagent based on the fluorescence of the energy transfer dye. Types of molecules and materials to which the dyes of the present invention may be attached to form a reagent include, but are not limited to, proteins, polypeptides, polysaccharides, nucleotides, nucleosides, oligonucleotides, lipids, solid supports, organic and inorganic polymers, and combinations and assemblages thereof, such as chromosomes, nuclei, living cells, such as bacteria, other microorganisms, mammalian cells, and tissues.

Preferred classes of reagents of the present invention are nucleotides, nucleosides and oligonucleotides which include an energy transfer dye of the invention. Examples of uses for nucleotide and nucleoside reagents include, but are not limited to, labeling oligonucleotides formed by enzymatic synthesis, e.g., nucleotide triphosphates used in the context of PCR amplification, Sanger-type oligonucleotide sequencing, and nick-translation reactions. Examples of uses for oligonucleotide reagents include, but are not limited to, as DNA sequencing primers, PCR primers, oligonucleotide hybridization probes, and the like.

One particular embodiment of the reagents are labelled nucleosides (NTP), such as cytosine, adenosine, guanosine, and thymidine, labelled with an energy transfer fluorescent dye of the present invention. These reagents may be used in a wide variety of methods involving oligonucleotide synthesis. Another related embodiment are labelled nucleotides, e.g., mono-, di- and triphosphate nucleoside phosphate esters. These reagents include, in particular, deoxynucleotide triphosphates (dNTP), such as deoxycytosine triphosphate, deoxyadenosine triphosphate, deoxyguanosine triphosphate, and deoxythymidine triphosphate, labelled with an energy transfer fluorescent dye of the present invention. These reagents may be used, for example, as polymerase substrates in the preparation of dye labelled oligonucleotides. These reagents also include labelled dideoxynucleotide triphosphates (ddNTP), such as dideoxycytosine triphosphate, dideoxyadenosine triphosphate, dideoxyguanosine triphosphate, and dideoxythymidine triphosphate, labelled with an energy transfer fluorescent dye of the present invention. These reagents may be used, for example, in dye termination sequencing.

Another embodiment of reagents are oligonucleotides which includes an energy transfer fluorescent dye of the present invention. These reagents may be used, for example, in dye primer sequencing.

As used herein, "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g. as described in Kornberg and Baker, *DNA Replication*, 2nd Ed. (Freeman, San Francisco, 1992). The term "nucleotide" as used herein refers to a phosphate ester of a nucleoside, e.g., mono, di and triphosphate esters, wherein the most common site of esterification is the hydroxyl group attached to the C-5 position of the pentose. "Analogs" in reference to nucleosides include synthetic nucleosides having modified base moieties and/or modified sugar moieties, e.g. described generally by Scheit, *Nucleotide Analogs* (John Wiley, N.Y., 1980). The terms "labeled nucleoside" and "labeled nucleotide" refer to nucleosides and nucleotides which are covalently attached to an energy transfer dye through a linkage.

As used herein, the term "oligonucleotide" refers to linear polymers of natural or modified nucleoside monomers, including double and single stranded deoxyribonucleosides, ribonucleosides, α-anomeric forms thereof, and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, $NH_4$, Na, and the like if such counterions are present. The oligonucleotides range in size form a few monomeric units, e.g. 8–40, to several thousands of monomeric units. Whenever an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

Nucleoside labeling can be accomplished using any of a large number of known nucleoside labeling techniques using known linkages, linking groups, and associated complementary functionalities. The linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not quench the fluorescence of the dye.

Preferably, the dyes are covalently linked to the 5-carbon of pyrimidine bases and to the 7-carbon of 7-deazapurine bases. Several suitable base labeling procedures have been reported that can be used with the invention, e.g. Gibson et al, *Nucleic Acids Research*, 15 6455–6467 (1987); Gebeyehu et al, *Nucleic Acids Research*, 15 4513–4535 (1987); Haralambidis et al, *Nucleic Acids Research*, 15 4856–4876 (1987); Nelson et al., *Nucleosides and Nucleotides*, 5(3) 233–241 (1986); Bergstrom, et al., *JACS*, 111 374–375 (1989); U.S. Pat. Nos. 4,855,225, 5,231,191, and 5,449,767, each of which is incorporated herein by reference.

Preferably, the linkages are acetylenic amido or alkenic amido linkages, the linkage between the dye and the nucleotide base being formed by reacting an activated N-hydroxysuccinimide (NHS) ester of the dye with an alkynylamino- or alkenylamino-derivatized base of a nucleotide. More preferably, the resulting linkage is 3-(carboxy)amino-1-propynyl or 3-amino-1-propyn-1-yl.

Several preferred linkages for linking the dyes of the invention to a nucleoside base are shown below.

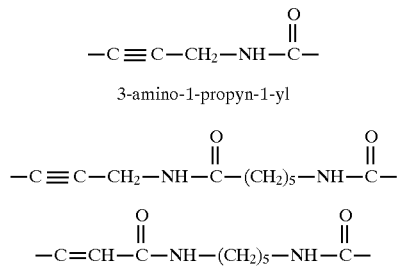

The synthesis of alkynylamino-derivatized nucleosides is taught by Hobbs et al. in European Patent Application No. 87305844.0, and Hobbs et al., *J. Org. Chem.*, 54 3420 (1989), which is incorporated herein by reference. Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture can be stirred for several hours, or until thin layer chromatography indicates consumption of the halodideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

The synthesis of oligonucleotides labelled with an energy transfer dye of the present invention can be accomplished using any of a large number of known oligonucleotide labeling techniques using known linkages, linking groups, and associated complementary functionalities. For example, labeled oligonucleotides may be synthesized enzymatically, e.g., using a DNA polymerase or ligase, e.g., Stryer, *Biochemistry*, Chapter 24, W.H. Freeman and Company (1981), or by chemical synthesis, e.g., by a phosphoramidite method, a phosphitetriester method, and the like, e.g., Gait, *Oligonucleotide Synthesis*, IRL Press (1990). Labels may be introduced during enzymatic synthesis utilizing labeled nucleotide triphosphate monomers, or introduced during chemical synthesis using labeled non-nucleotide or nucleotide phosphoramidites, or may be introduced subsequent to synthesis.

Generally, if the labeled oligonucleotide is made using enzymatic synthesis, the following procedure may be used. A template DNA is denatured and an oligonucleotide primer is annealed to the template DNA. A mixture of deoxynucleotide triphosphates is added to the reaction including dGTP, dATP, dCTP, and dTTP where at least a fraction of one of the deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase strand synthesis. In an alternative enzymatic synthesis method, two primers are used instead of one, one primer complementary to the+strand and the other complementary to the - strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols*, Innis et al. eds., Academic Press (1990).

Generally, if the labeled oligonucleotide is made using a chemical synthesis, it is preferred that a phosphoramidite method be used. Phosphoramidite compounds and the phosphoramidite method of polynucleotide synthesis are preferred in synthesizing oligonucleotides because of the efficient and rapid coupling and the stability of the starting materials. The synthesis is performed with the growing oligonucleotide chain attached to a solid support, so that excess reagents, which are in the liquid phase, can be easily removed by filtration, thereby eliminating the need for purification steps between cycles.

In view of the utility of phosphoramidite reagents in labeling nucleosides and oligonucleotides, the present invention also relates to phosphoramidite compounds which include an energy transfer dye of the present invention.

Detailed descriptions of the chemistry used to form oligonucleotides by the phosphoramidite method are provided in Caruthers et al., U.S. Pat. No. 4,458,066; Caruthers et al., U.S. Pat. No. 4,415,732; Caruthers et al., *Genetic Engineering*, 4 1–17 (1982); *Users Manual Model* 392 and 394 Polynucleotide Synthesizers, pages 6–1 through 6–22, Applied Biosystems, Part No. 901237 (1991), each of which are incorporated by reference in their entirety.

The following briefly describes the steps of a typical oligonucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55° C.

Any of the phosphoramidite nucleoside monomers may be dye-labeled phosphoramidites. If the 5'-terminal position of the nucleotide is labeled, a labeled non-nucleotidic phosphoramidite of the invention may be used during the final condensation step. If an internal position of the oligonucleotide is to be labeled, a labeled nucleotidic phosphoramidite of the invention may be used during any of the condensation steps.

Subsequent to their synthesis, oligonucleotides may be labeled at a number of positions including the 5'-terminus. See *Oligonucleotides and Analogs*, Eckstein ed., Chapter 8, IRL Press (1991) and Orgel et al., *Nucleic Acids Research* 11(18) 6513 (1983); U.S. Pat. No. 5,118,800, each of which are incorporated by reference Oligonucleotides may also be labeled on their phosphodiester backbone (*Oligonucleotides and Analogs*, Eckstein ed., Chapter 9) or at the 3'-terminus (Nelson, *Nucleic Acids Research* 20(23) 6253–6259, and U.S. Pat. Nos. 5,401,837 and 5,141,813, both patents hereby incorporated by reference. For a review of oligonucleotide labeling procedures see R. Haugland in *Excited States of Biopolymers*, Steiner ed., Plenum Press, N.Y. (1983).

In one preferred post-synthesis chemical labeling method an oligonucleotide is labeled as follows. A dye including a carboxy linking group is converted to the n-hydroxysuccinimide ester by reacting with approximately 1 equivalent of 1,3-dicyclohexylcarbodiimide and approximately 3 equivalents of n-hydroxysuccinimide in dry ethyl acetate for 3 hours at room temperature. The reaction mixture is washed with 5 % HCl, dried over magnesium sulfate, filtered, and concentrated to a solid which is resuspended in DMSO. The DMSO dye stock is then added in excess (10–20×) to an aminohexyl derivatized oligonucleotide in 0.25M bicarbonate/carbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylamine acetate (TEAA). The fraction containing the crude labeled oligonucleotide is further purified by reverse phase HPLC employing gradient elution.

III. Methods Employing Dyes And Reagents Of The Present Invention

The energy transfer dyes and reagents of the present invention may be used in a wide variety of methods for detecting the presence of a component in a sample by labelling the component in the sample with a reagent containing the dye. In particular, the energy transfer dyes and reagents of the present invention are well suited for use in methods which combine separation and fluorescent detection techniques, particularly methods requiring the simultaneous detection of multiple spatially-overlapping analytes. For example, the dyes and reagents are particularly well suited for identifying classes of oligonucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-oligonucleotide conjugates by electrophoresis.

Classes of oligonucleotides can arise in a variety of contexts. In a preferred category of methods referred to herein as "fragment analysis" or "genetic analysis" methods, labeled oligonucleotide fragments are generated through template-directed enzymatic synthesis using labeled primers or nucleotides, e.g., by ligation or polymerase directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of oligonucleotides are separated simultaneously and the different classes are distinguished by spectrally resolvable labels.

One such fragment analysis method is amplified fragment length polymorphisim detection (AmpFLP) and is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled oligonucleotide PCR primer, or by utilizing labeled nucleotide triphosphates in the PCR.

Another fragment analysis method is nick translation. Nick translation involves a reaction to replace unlabeled nucleotide triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments by using a dye-labeled PCR primer.

Another exemplary fragment analysis method is DNA sequencing. In general, DNA sequencing involves an extension/termination reaction of an oligonucleotide primer. Included in the reaction mixture are deoxynucleotide triphosphates (dNTPs) which are used to extend the primer. Also included in the reaction mixture is at least one dideoxynucleotide triphosphate (ddNTP) which when incorporated onto the extended primer prevents the further extension of the primer. After the extension reaction has been terminated, the different termination products that are formed are separated and analyzed in order to determine the positioning of the different nucleosides.

Fluorescent DNA sequencing may generally be divided into two categories, "dye primer sequencing" and "dye terminator sequencing". In dye primer sequencing, a fluorescent dye is incorporated onto the primer being extended. Four separate extension/termination reactions are then run in parallel, each extension reaction containing a different dideoxynucleotide triphosphate (ddNTP) to terminate the extension reaction. After termination, the reaction products are separated by gel electrophoresis and analyzed. See, for example, Ansorge et al., Nucleic Acids Res. 15 4593–4602 (1987).

In one variation of dye primer sequencing, different primers are used in the four separate extension/termination reactions, each primer containing a different spectrally resolvable dye. After termination, the reaction products from the four extension/termination reactions are pooled, electrophoretically separated, and detected in a single lane. See, for example, Smith et al., Nature 321 674–679 (1986). Thus, in this variation of dye primer sequencing, by using primers containing a set of spectrally resolvable dyes, products from more than one extension/termination reactions can be simultaneously detected.

In dye terminator sequencing, a fluorescent dye is attached to each of the dideoxynucleotide triphosphates. An extension/termination reaction is then conducted where a primer is extended using deoxynucleotide triphosphates until the labelled dideoxynucleotide triphosphate is incorporated into the extended primer to prevent further extension of the primer. Once terminated, the reaction products for each dideoxynucleotide triphosphate are separated and detected. In one embodiment, separate extension/termination reactions are conducted for each of the four dideoxynucleotide triphosphates. In another embodiment, a single extension/termination reaction is conducted which contains the four dideoxynucleotide triphosphates, each labelled with a different, spectrally resolvable fluorescent dye.

Thus according to one aspect of the invention, a method is provided for conducting dye primer sequencing using one or more oligonucleotide reagents of the present invention. According to this method, a mixture of extended labelled Primers are formed by hybridizing a nucleic acid sequence with a fluorescently labelled oligonucleotide primer in the presence of deoxynucleotide triphosphates, at least one dideoxynucleotide triphosphate and a DNA polymerase. The fluorescently labelled oligonucleotide primer includes an oligonucleotide sequence complementary to a portion of the nucleic acid sequence being sequenced, and an energy transfer fluorescent dye attached to the oligonucleotide.

According to the method, the DNA polymerase extends the primer with the deoxynucleotide triphosphates until a dideoxynucleotide triphosphate is incorporated which terminates extension of the primer. After termination, the mixture of extended primers are separated. The sequence of the nucleic acid sequence is then determined by fluorescently detecting the mixture of extended primers formed.

In a further embodiment of this method, four dye primer sequencing reactions are run, each primer sequencing reaction including a different fluorescently labelled oligonucleotide primer and a different dideoxynucleotide triphosphate (ddATP, ddCTP, ddGTP and ddTTP). After the four dye primer sequencing reactions are run, the resulting mixtures of extended primers may be pooled. The mixture of extended primers may then be separated, for example by electrophoresis and the fluorescent signal from each of the four different fluorescently labelled oligonucleotide primers detected in order to determine the sequence of the nucleic acid sequence.

According to a further aspect of the invention, a method is provided for conducting dye terminator sequencing using one or more dideoxynucleotide triphosphates labelled with an energy transfer dye of the present invention. According to this method, a mixture of extended primers are formed by hybridizing a nucleic acid sequence with an oligonucleotide primer in the presence of deoxynucleotide triphosphates, at least one fluorescently labelled dideoxynucleotide triphosphate and a DNA polymerase. The fluorescently labelled dideoxynucleotide triphosphate includes a dideoxynucleotide triphosphate labelled with an energy transfer fluorescent dye of the present invention.

According to this method, the DNA polymerase extends the primer with the deoxynucleotide triphosphates until a fluorescently labelled dideoxynucleotide triphosphate is incorporated into the extended primer. After termination, the mixture of extended primers are separated. The sequence of the nucleic acid sequence is then determined by detecting the fluorescently labelled dideoxynucleoside attached to the extended primer.

In a further embodiment of this method, the step of forming a mixture of extended primers includes hybridizing the nucleic acid sequence with four different fluorescently labelled dideoxynucleotide triphosphates, i.e., a fluorescently labelled dideoxycytosine triphosphate, a fluorescently labelled dideoxyadenosine triphosphate, a fluorescently labelled dideoxyguanosine triphosphate, and a fluorescently labelled dideoxythymidine triphosphate.

In each of the above-described fragment analysis methods, the labeled oligonucleotides are preferably separated by electrophoretic procedures, e.g. Gould and Matthews, cited above; Rickwood and Hames, Eds., *Gel Electrophoresis of Nucleic Acids: A Practical Approach*, (IRL Press Limited, London, 1981); or Osterman, *Methods of Protein and Nucleic Acid* Research, Vol. 1 Springer-Verlag, Berlin, 1984). Preferably the type of electrophoretic matrix is crosslinked or uncrosslinked polyacrylamide having a concentration (weight to volume) of between about 2–20 weight percent. More preferably, the polyacrylamide concentration is between about 4–8 percent. Preferably in the context of DNA sequencing in particular, the electrophoresis matrix includes a strand separating, or denaturing, agent, e.g., urea, formamide, and the like. Detailed procedures for constructing such matrices are given by Maniatis et al., "Fractionation of Low Molecular Weight DNA and RNA in Polyacrylamide Gels Containing 98% Formamide or 7M Urea," in *Methods in Enzymology*, 65 299–305 (1980); Maniatis et al., "Chain Length Determination of Small Double and Single-Stranded DNA Molecules by Polyacrylamide Gel Electrophoresis,"*Biochemistry*, 14 3787–3794 (1975); Maniatis et al., *Molecular Cloning: A Laboratory Manual* (Cold Spring Harbor Laboratory, N.Y., 1982), pgs. 179–185; and ABI PRISM™377 DNA *Sequencer Users Manual, Rev. A*, January 1995, Chapter 2 (p/n 903433, The Perkin-Elmer Corporation, Foster City, Calif.), each of which are incorporated by reference. The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following matrix: 6 percent polyacrylamide made from 19 parts to 1 part acrylamide to bis-acrylamide, formed in a Tris-borate EDTA buffer at pH 8.3.

After electrophoretic separation, the dye-oligonucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or an the 532 emission line of a neodymium solid-state YAG laser. Several argon ion lasers are available commercially which lase simultaneously at these lines, e.g. Cyonics, Ltd. (Sunnyvale, Calif.) Model 2001, or the like.

The fluorescence is then detected by a light-sensitive detector, e.g., a photomultiplier tube, a charged coupled device, or the like.

IV. Kits Incorporating The Energy Transfer Dyes

The present invention also relates to kits having combinations of energy transfer fluorescent dyes and/or reagents. In one embodiment, the kit includes at least two spectrally resolvable energy transfer dyes according to the present invention. In this kit, the energy transfer dyes preferably include the same donor dye so that a single light source is needed to excite the dyes.

In another embodiment, the kit includes dideoxycytosine triphosphate, dideoxyadenosine triphosphate, dideoxyguanosine triphosphate, and dideoxythymidine triphosphate, each dideoxynucleotide triphosphate labelled with an energy transfer dye according to the present invention. In one embodiment, each energy transfer dye is spectrally resolvable from the other energy transfer dyes attached to the other dideoxynucleotide triphosphates. In this kit, the energy transfer dyes preferably include the same first xanthene dye.

In yet another embodiment, the kit includes at least two oligonucleotides, each oligonucleotide including an energy transfer dye according to the present invention. In one embodiment, each oligonucleotide contains an energy transfer dye which is spectrally resolvable from the energy transfer dyes attached to the other oligonucleotides. In another embodiment, the kit includes at least four oligonucleotides which each contain a spectrally resolvable energy transfer dye.

The energy transfer fluorescent dyes and their use in DNA sequencing is illustrated by the following examples. Further objectives and advantages other than those set forth above will become apparent from the examples.

Examples 1. Synthesis of 5TMR-B-CF

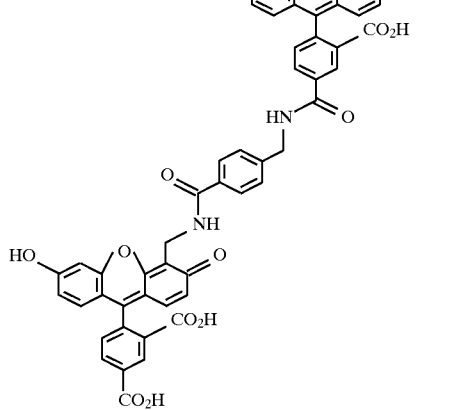

5TMR-B-CF was synthesized from 5TMR NHS and 4'-aminomethyl-5-carboxyfluorescein according to the reaction sequences described in Examples 1A–C. 5TMR-B-CF was then converted to 5TMR-B-CF-NHS according to the reaction sequence described in 1D so that the dye could be coupled to a nucleoside, nucleotide or oligonucleotide primer.

A. Synthesis of 5-TMR-B

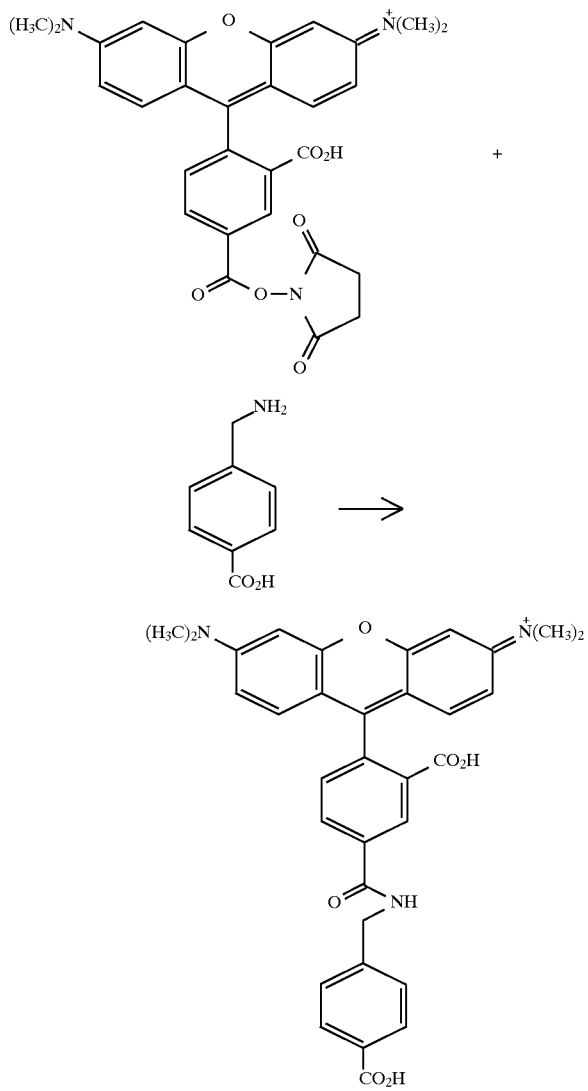

A mixture of 4-aminomethylbenzoic acid (3 mg, 19 μmol), 5-TMR NHS (5 mg, 9 μmol) and triethylamine (20 μL) was suspended in dimethylformamide (DMF, 200 μL) in a 1.5-mL eppendorf tube. The mixture was heated to 60° C. for 10 minutes. Reaction progress was monitored by thin layer chromatography (TLC) on silica gel with elution with a 400/30/10 mixture of dichloromethane, methanol and acetic acid. The insoluble 4-aminomethylbenzoic acid was separated by centrifugation and the DMF solution was decanted into 5% HCl (1 mL). The insoluble 5TMR-B was separated by centrifugation, washed with 5% HCl (2×1 mL) and dried in a vacuum centrifuge. The product was dissolved in DMF (200 μL) and used to prepare 5TMR-B-NHS.

B. Synthesis of 5-TMR-B-NHS

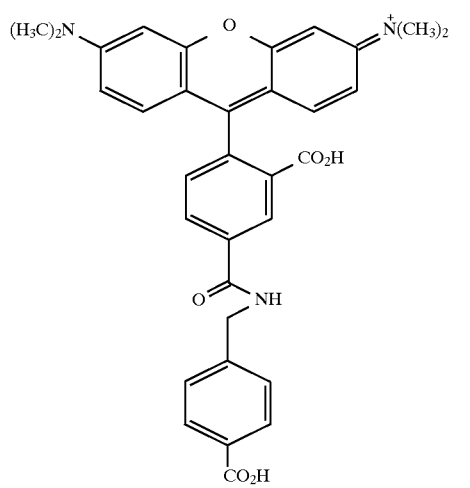

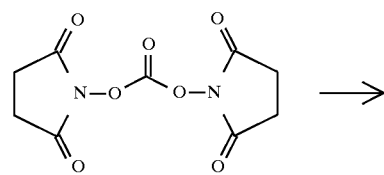

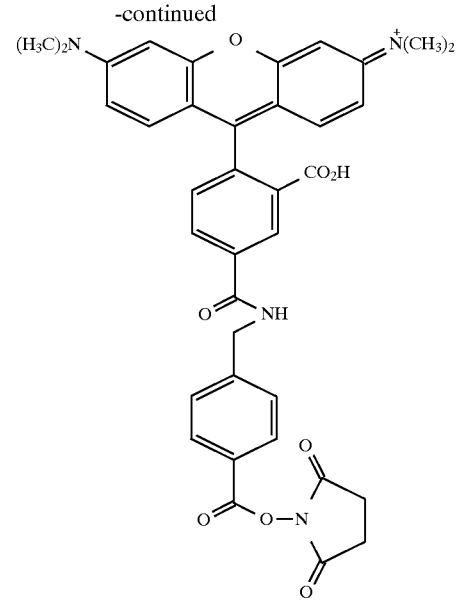

A solution of 5TMR-B in DMF (125 μL), diisopropylethylamine (10 μL) and disuccinimidylcarbonate (10 mg) was combined in a 1.5-mL eppendorf tube and heated to 60° C. The reaction progress was monitored by TLC on silica gel with elution with a 600/60/16 mixture of dichloromethane, methanol and acetic acid. After five minutes, the reaction appeared to be complete. The solution was diluted into methylene chloride (3 mL) and washed with 250 mM carbonate/bicarbonate buffer (pH 9, 4×1 mL), dried ($Na_2SO_4$) and concentrated to dryness on a vacuum centrifuge. The solid was dissolved in DMF (100 μL). The yield was determined by diluting an aliquot into pH 9 buffer and measuring the absorbance at 552 nm. Using an extinction coefficient of 50,000 $cm^{-1}$ $M^{-1}$, the concentration of 5TMR-B-NHS was 4.8 mM. Yield from 5TMR NHS was 8%.

C. Synthesis of 5TMR-B-CF

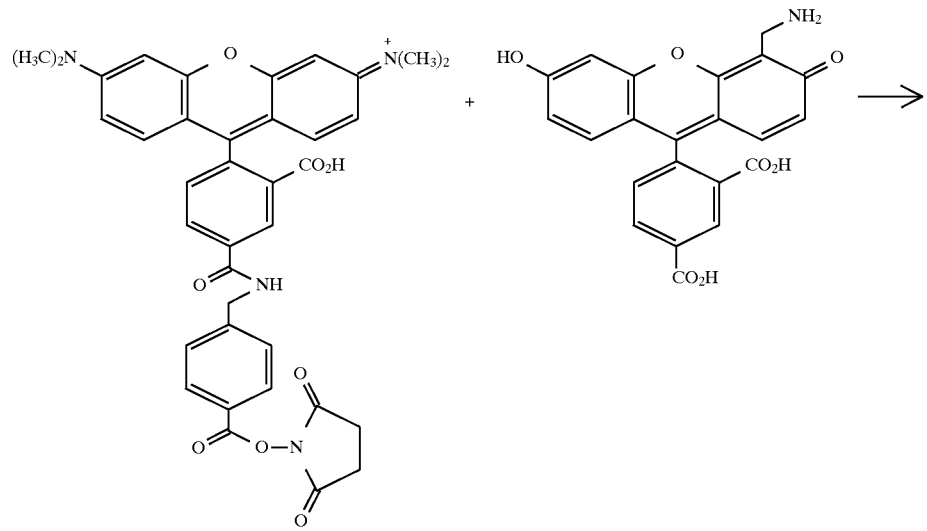

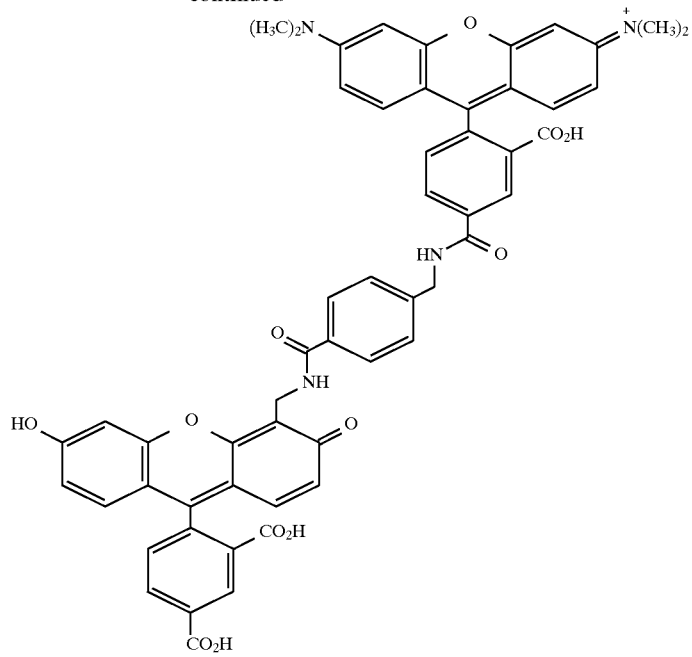

A solution of 5TMR-B-NHS (1 μmol in 250 μL DMF) was combined with a solution of 4'-aminomethyl-5-carboxyfluorescein (CF, 2.2 μmol in 100 μL DMSO) and triethylamine (20 μL) in a 1.5-mL eppendorf tube. The reaction was monitored by HPLC using a C8 reverse-phase column with a gradient elution of 15% to 35% acetonitrile vs. 0.1M triethylammonium acetate. HPLC analysis indicated the 5TMR-B-NHS was consumed, leaving the excess, unreacted CF. The reaction was diluted with 5% HCl (1 mL) and the product separated by centrifugation, leaving the unreacted CF in the aqueous phase. The solid was washed with 5% HCl (4×1 mL), dried in a vacuum centrifuge and taken up in DMF (300 μL). The yield was quantitative.

D. Synthesis of 5-TMR-B-CF-NHS

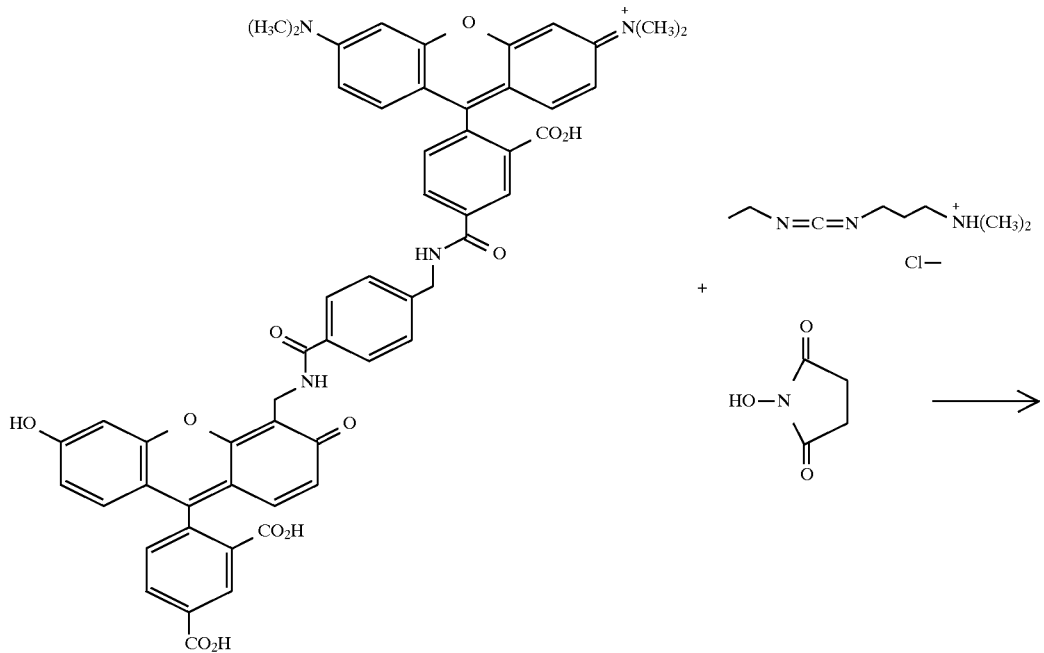

-continued

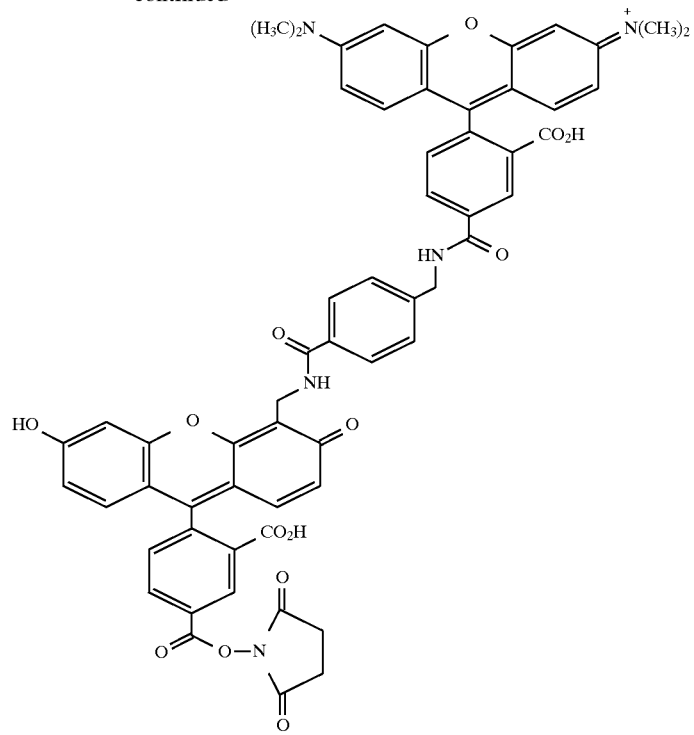

A solution of 5TMR-B-CF (0.6 μmol in 100 μL DMF), 1-(3-dimethylaminopropyl)-3-ethylcarbodiimide hydrochloride (DEC, 2 mg) and N-hydroxysuccinimide (4 mg) were combined in a 1.5-mL eppendorf tube. The mixture was sonicated briefly and heated to 60° C. The reaction was monitored by TLC on silica gel with elution with a 600/60/16 mixture of dichloromethane, methanol and acetic acid. The reaction was complete in 30 minutes and diluted with 5% HCl. The product was separated by centrifugation and dried in a vacuum centrifuge. The activated dye was dissolved in DMF (20 μL).

2. Synthesis of 5ROX-CF

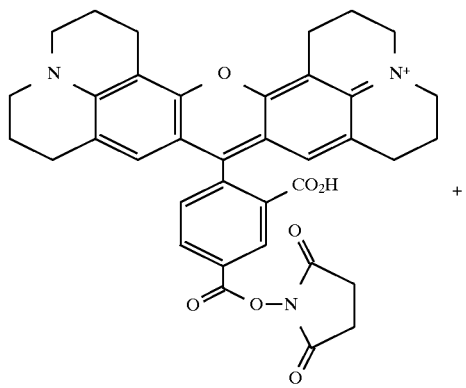

+

-continued

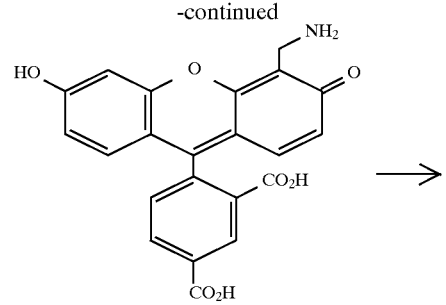

→

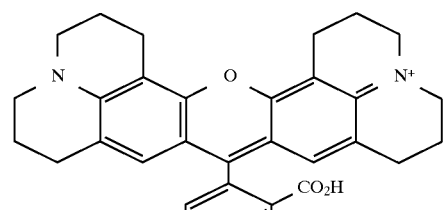

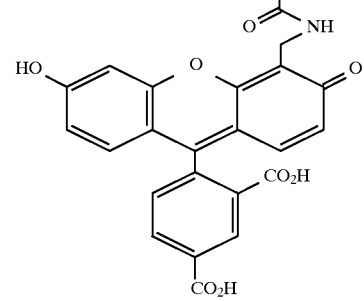

A solution of 5ROX NHS (2 μmol in 100 μL DMSO) was mixed with CF (2 μmol in 100 μL DMSO) and triethylamine (10 μL). The reaction was followed by HPLC on a C8 reverse phase column using a gradient elution of 20% to 40% acetonitrile vs. 0.1M TEM. The reaction was diluted into 5% HCl (1 mL) and the product collected by centrifugation, washed with 5% HCl (1×1 mL) and dried in a vacuum centrifuge. The product was taken up in DMF (200 μL).

3. Synthesis of Cy5-CF

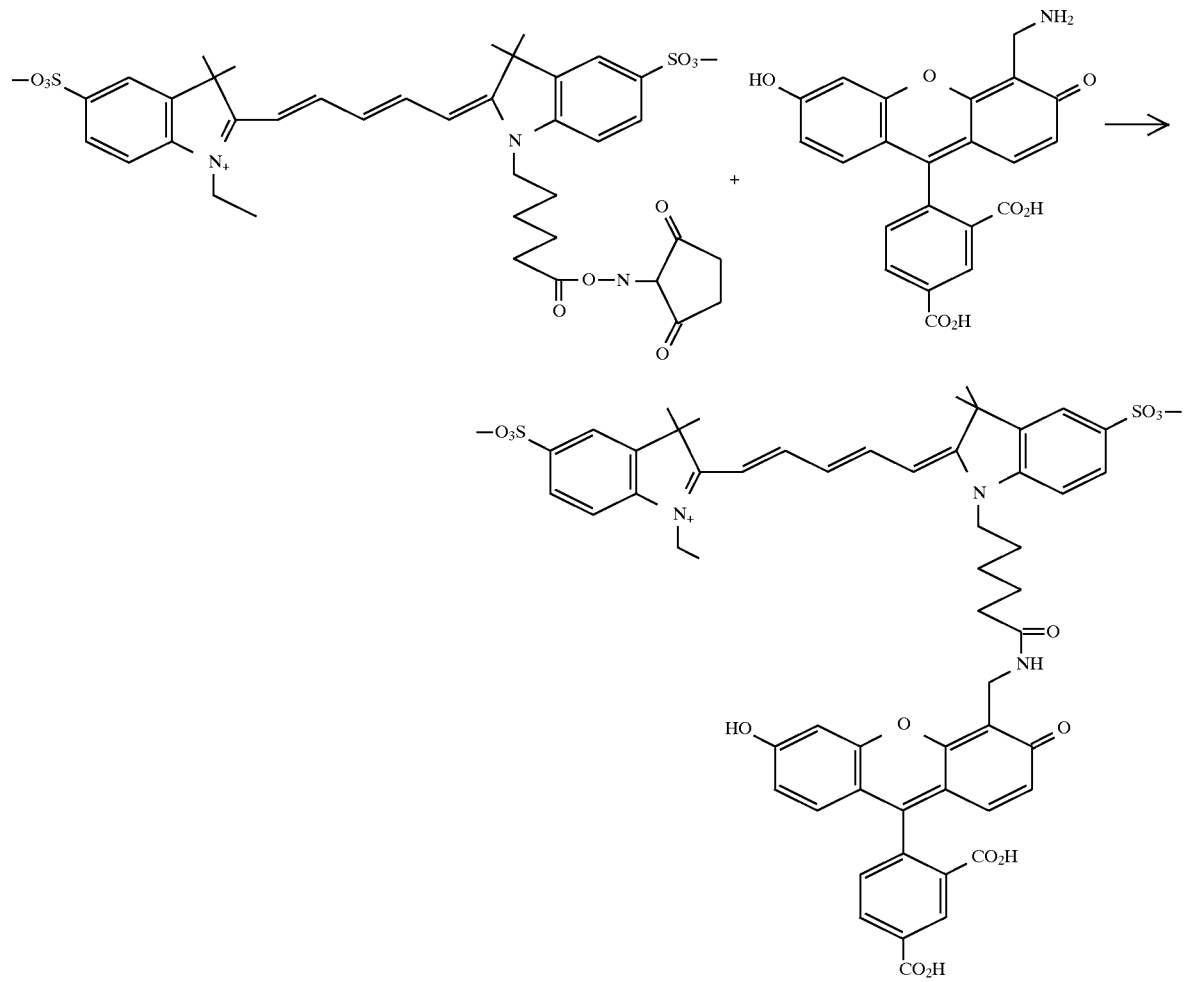

A solution of CF (0.4 μmol in 20 μL CMSO) and triethylamine (2 μL) was added to monoCy5 NHS (approximately 0.3 μmol). The reaction was followed by HPLC on a C8 reverse phase column using a gradient elution of 10% to 30% acetonitrile vs. 0.1M TEAA. The reaction was diluted into 5% HCl (1 mL) and the product collected by centrifugation, washed with 5% HCl (1×1 mL) and dried in a vacuum centrifuge. The product was taken up in DMF (100 μL).

4. Comparison Of Fluorescence Strength of Energy Transfer Dyes

The following example compares the fluorescence emission strength of a series of energy transfer dyes according to the present invention. Dye solutions of 5TMR, 6TMR-CF, 5TMR-gly-CF, 5TMR-CF, 5TMR-B-CF, 5TMR-gly-5AMF, 5TMR-5AMF and 5TMR-lys-5FAM were measured in 1×TBE/8M urea. Each dye solution had an optical density of 0.1 at 560 nm and was excited at 488 nm.

TABLE 7
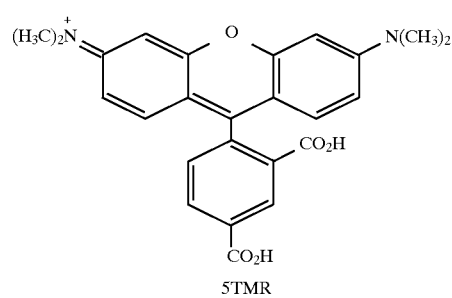
5TMR
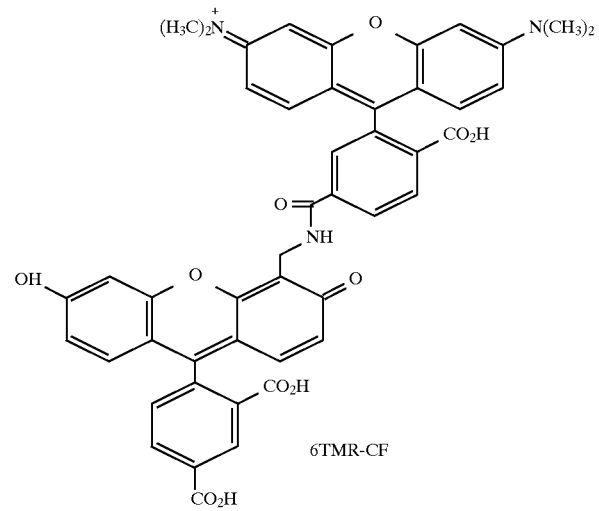
6TMR-CF
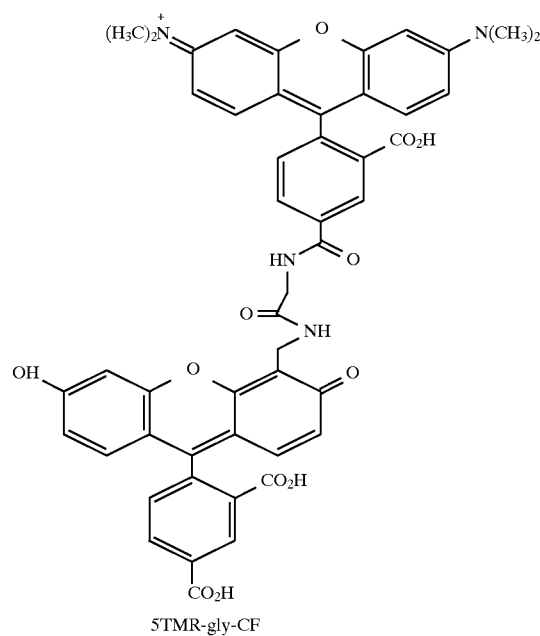
5TMR-gly-CF

TABLE 7-continued
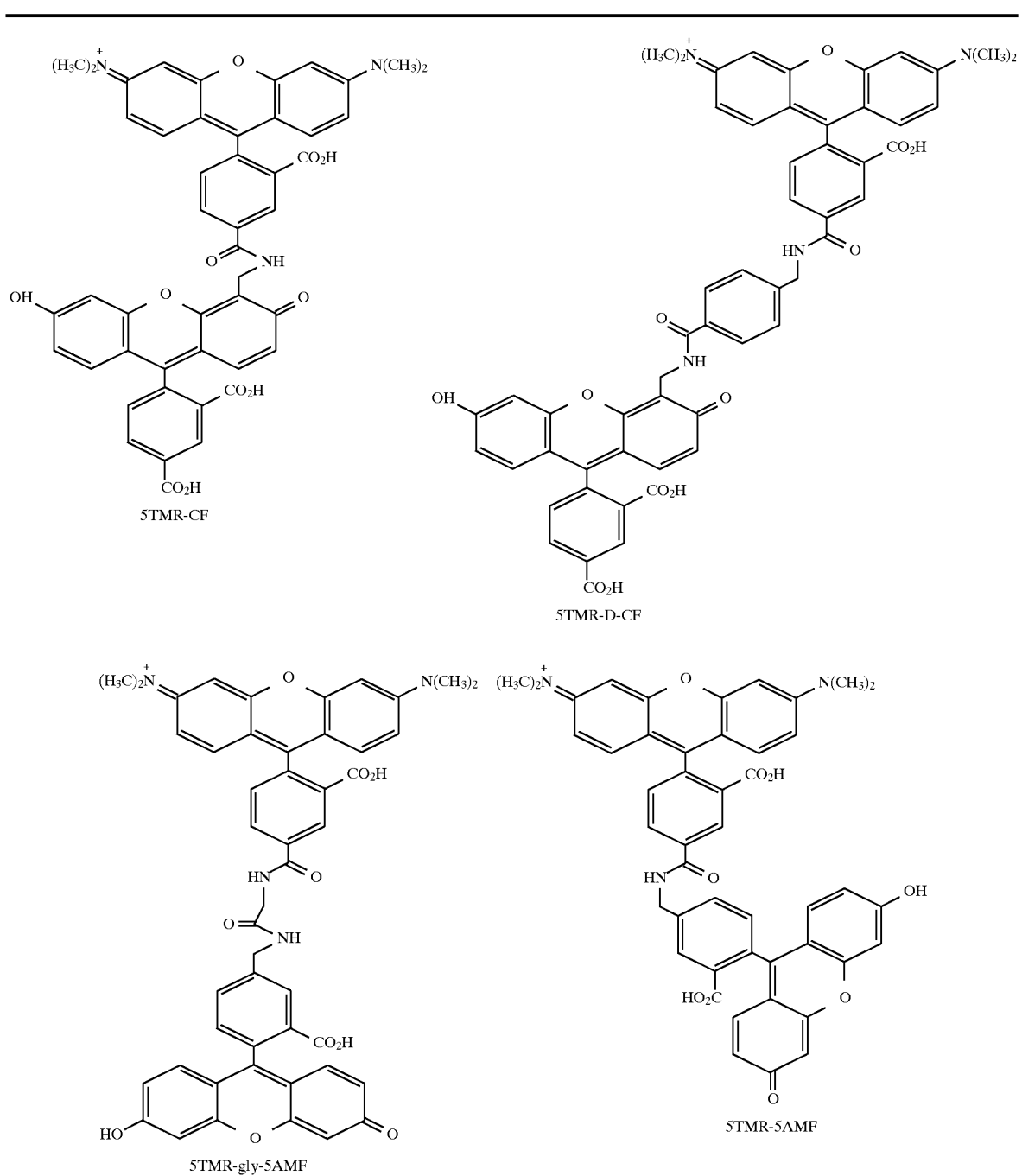

TABLE 7-continued

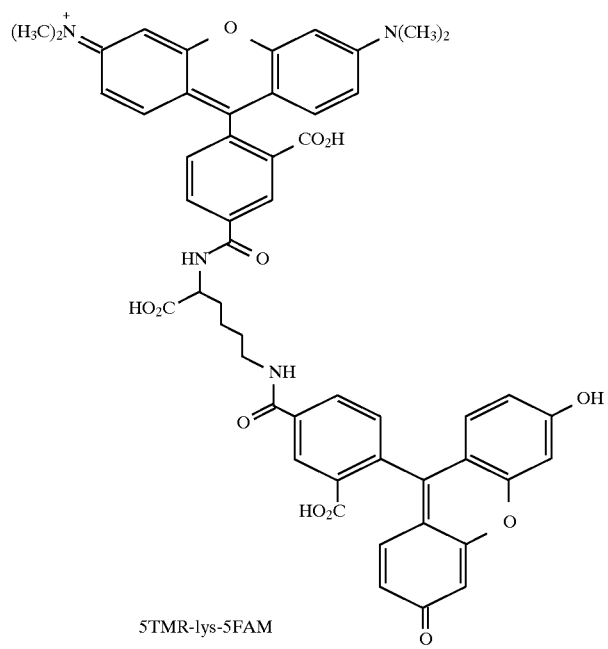

5TMR-lys-5FAM

The structures of each of these dyes is illustrated in Table 7. FIG. 2 provides a bar graph of the relative fluorescence of each of these dyes.

As can be seen from FIG. 2, energy transfer dyes where the linker is attached to the acceptor at the 5 ring position (5TMR-CF and 5-TMR-B-CF were found to exhibit significantly stronger fluorescence than the acceptor dye itself or when the acceptor dye is linked at the 6 ring position (6TMR-CF). As also can be seen from FIG. 2, energy transfer dyes where the linker has the formula $R_1XC(O)R_2$ where $R_2$ is benzene (5TMR-B-CF) were found to have significantly enhanced fluorescence as compared to the dye where the linker has the formula —$CH_2NHCO$— (5TMR-CF) or —$CH_2NHCOCH_2NHCO$— (5TMR-gly-5AMF).

As can also be seen from FIG. 2, energy transfer dyes where the linker is attached to both the donor and acceptor at the 5 ring position (5TMR-5AMF and 5TMR-gly-5AMF) were found to have significant fluorescence. Interestingly, the use of a lysine linker was found not to result in appreciable energy transfer between the donor and acceptor.

5. Dye Primer Sequencing Using Energy Transfer Dye

Figure 5:
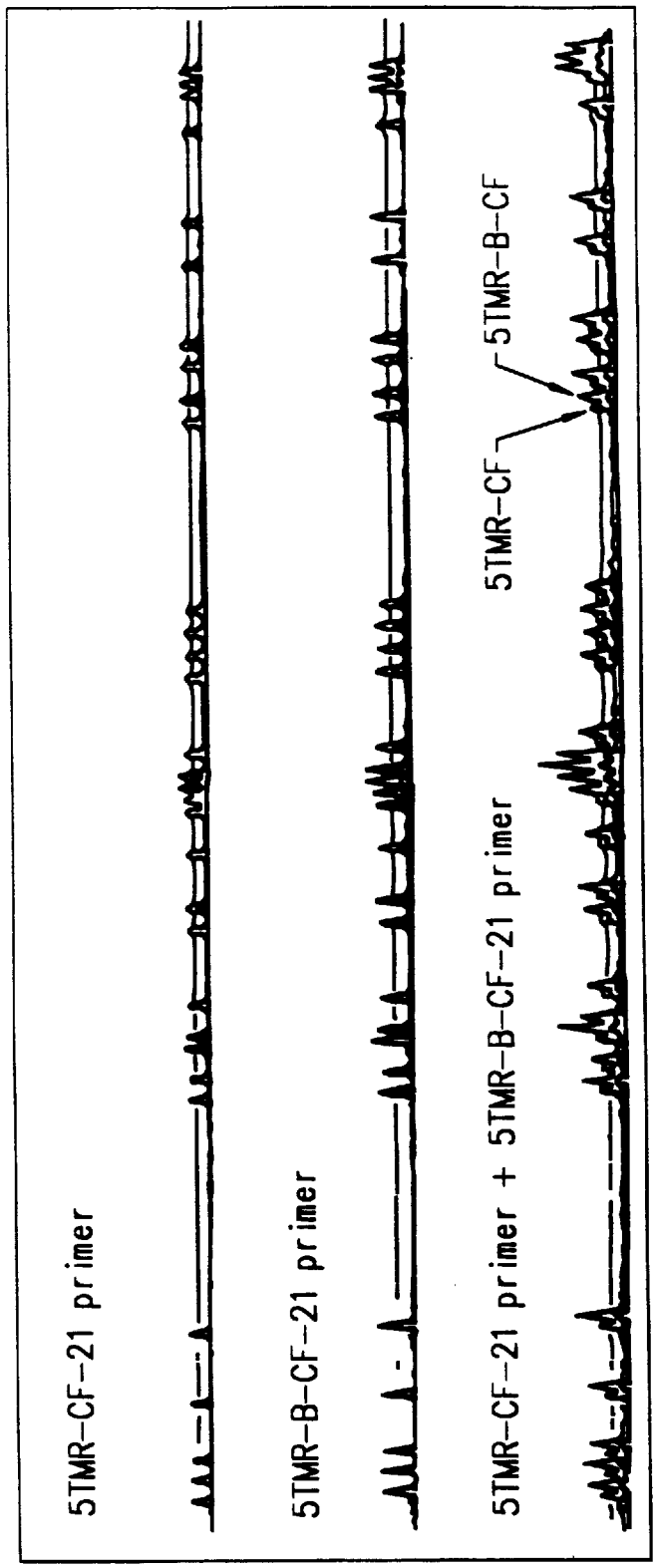
FIG. 5 is a plot of a mixture of labelled oligonucleotides generated during dye primer sequencing using 5TMR-CF and 5TMR-B-CF labelled primers.

In this example, dye primer sequencing was performed on M13 (SEQ. ID. NO.: 1) in order to compare the relative brightness of 5TMR-CF and 5TMR-B-CF labelled oligonucleotides. In this example, dye primer sequencing was performed according to the ABl PRISM™377 DNA Sequencer User's Manual, Rev. B, January 1995, Chapter 2 (p/n 402114, The Perkin-Elmer Corporation, Foster City, Calif.). 5TMR-CF and 5TMR-B-CF were each attached to the 5' end of M13–21 primer (SEQ. ID. NO.:2). Equimolar solutions of each primer were mixed with the M13 (SEQ. ID. NO.: 1) and sequenced with a single dideoxy nucleotide mixture (ddA/dNTP) and Taq FS. A plot of the resulting mixture of oligonucleotides that were detected using 5TMR-CF and 5TMR-B-CF labelled primers is presented in FIG. 5. As can be seen from FIG. 5, oligonucleotides labelled with 5TMR-B-CF are brighter than oligonucleotides labelled with 5TMR-CF. As can also be seen from FIG. 5, the mobility of oligonucleotides labelled with 5TMR-B-CF are about one nucleotide slower than the oligonucleotides labelled with 5TMR-CF.

6. Dye Primer Sequencing Using Four Dyes

Figure 6:
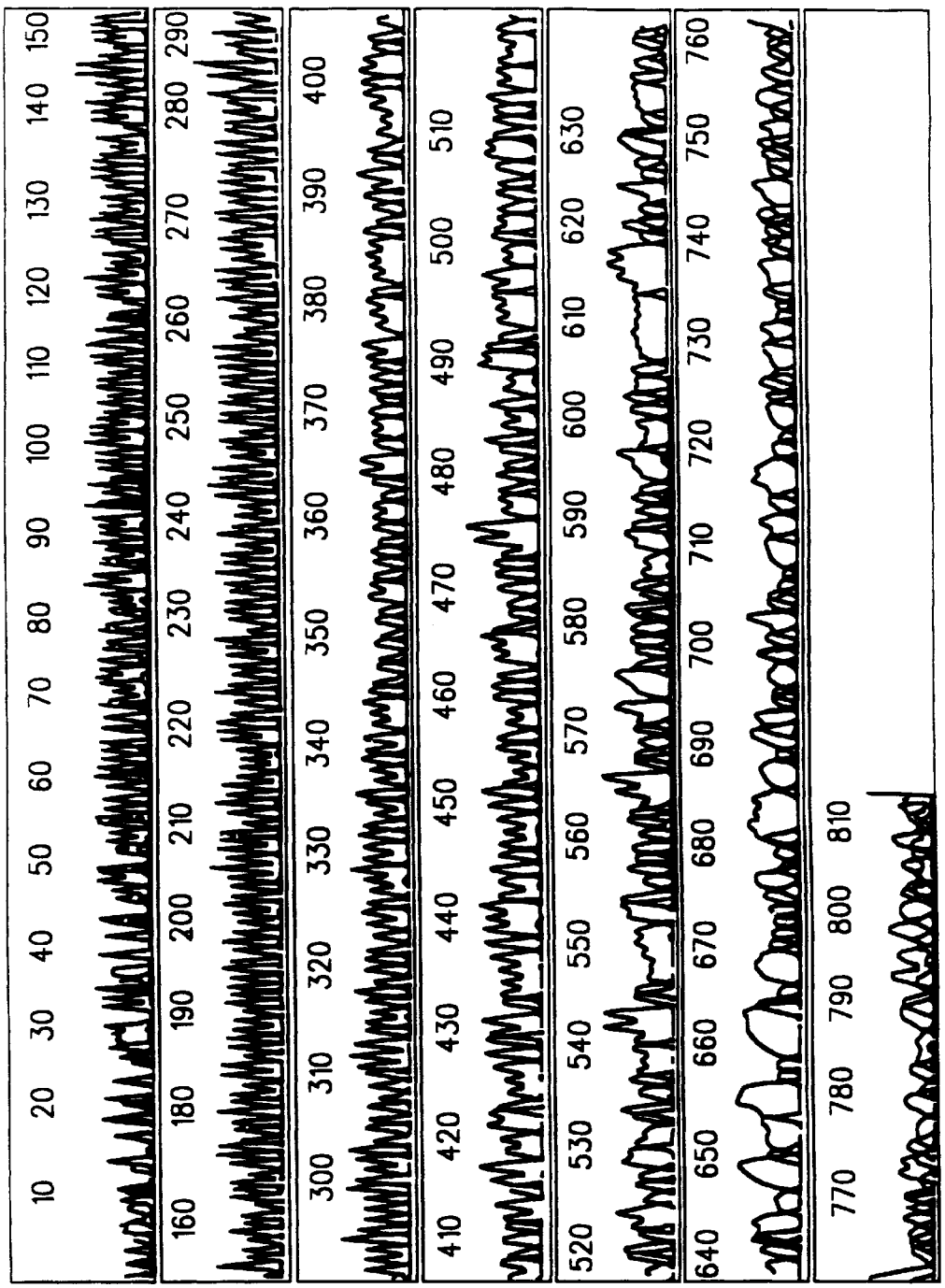
FIG. 6 is a four color plot of dye primer sequencing using a four dye set including 3-carboxy-R110, 5-carboxy-R6G, 5TMR-CF and 5TMR-B-CF.

Dye primer sequencing was performed on the M13 (SEQ. ID. NO.: 1) using a set of four dyes attached to the M13–21 primer (SEQ. ID. NO. 2) as described in Example 5. FIG. 6 is a four color plot of the dye labelled oligonucleotides produced from the sequencing. The peak for cytosine corresponds to the fluorescence of 5-carboxy-R110. The peak for adenosine corresponds to the fluorescence of 5-carboxy-R6G. The peak for guanosine corresponds to the fluorescence of TMR-B-CF. The peak for thymidine corresponds to the fluorescence of ROX-CF.

As can be seen from FIG. 6, each of the dye labelled oligonucleotides exhibit significant fluorescence intensity. In addition, the different dye labelled oligonucleotides exhibit sufficiently similar mobility so that good resolution of the series of peaks is achieved.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following s and their equivalents.

What is claimed is:

1. An energy transfer fluorescent dye comprising:

a donor dye with a xanthene ring structure, the donor dye absorbing light at a first wavelength and emitting excitation energy in response;

an acceptor dye which is capable of absorbing the excitation energy emitted by the donor dye and fluorescing at a second wavelength in response; and a linker attaching the donor dye to the acceptor dye, the linker having a 4' end which includes a $R_1XC(O)R_2$ group where $R_1$ is a $C_{1-5}$ alkyl attached to a 4' ring position on the xanthene ring structure of the donor dye, X is selected from the group consisting of NH, sulfur and oxygen, C(O) is a carbonyl group, and $R_2$ attaches the linker to the acceptor dye and includes a functional group which is attached to the carbonyl carbon selected from the group consisting of an alkene, diene, alkyne, a five and six membered ring having at least one unsaturated bond and a fused ring structure.

2. The energy transfer dye according to claim 1 wherein the donor dye is a member of a class of dyes selected from the group consisting of fluorescein, rhodamine and asymmetric benzoxanthene dyes.

3. The energy transfer dye according to claim 1 wherein the donor dye is selected from the group consisting of 5-carboxyfluorescein, 4,7-dichlorofluorescein dyes, asymmetric benzoxanthene dyes, rhodamine, 5-carboxyrhodamine, N,N,N',N'-tetramethyl 5-carboxyrhodamine, 5-carboxy R110, and 5-carboxy R6G.

4. The energy transfer dye according to claim 1 wherein the acceptor dye is a member of a class of dyes selected from the group consisting of xanthene, cyanine, phthalocyanine and squaraine dyes.

5. The energy transfer dye according to claim 1 wherein the acceptor dye is selected from the group consisting of 4,7-dichlorofluorescein dyes, asymmetric benzoxanthene dyes, rhodamine, 5-carboxyrhodamine, N,N,N',N'-tetramethyl 5-carboxyrhodamine, 5-carboxy R110, 5-carboxy R6G, 5-carboxy-X-rhodamine and Cy5.

6. The energy transfer dye according to claim 1 wherein the functional group attached to the carbonyl carbon is selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine, oxazine, indene, benzofuran, thionaphthene, indole and naphthalene.

7. The energy transfer dye according to claim 1 wherein the acceptor is a member of the xanthene class of dyes.

8. The energy transfer dye according to claim 7 wherein the acceptor has the general structure

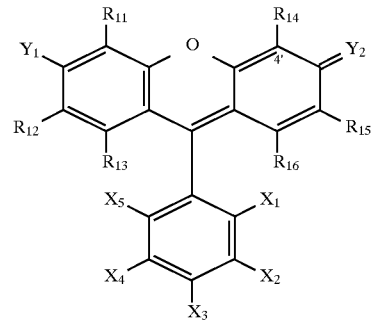

wherein:

$Y_1$ and $Y_2$ are each independently selected from the group consisting of hydroxyl, oxygen, iminium and amine;

$R_{11}$–$R_{16}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1$, $X_2$, $X_4$ and $X_5$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof; and $X_3$ is the linker.

9. The energy transfer dye according to claim 8 wherein the end of the linker attached to the acceptor includes a carbonyl group which forms part of an ester, ketone, amide or thioester functional group, the linker being attached to the acceptor by the carbon of the carbonyl group.

10. An energy transfer fluorescent dye comprising:

a donor dye with a xanthene ring structure the donor dye absorbing light at a first wavelength and emitting excitation energy in response;

an acceptor dye which is a member of a class of dyes selected from the group consisting of xanthene, cyanine, phthalocyanine and squaraine and is capable of absorbing the excitation energy emitted by the donor dye and fluorescing at a second wavelength in response, the acceptor having an emission maximum that is greater than about 600 nm or at least about 100 nm greater than the absorbance maximum of the donor dye; and a linker attaching the donor dye to the acceptor dye which his a sufficiently short length that the acceptor dye absorbs substantially all of the excitation energy emitted by the donor dye.

11. The energy transfer dye according to claim 10 wherein the linker is attached to the donor dye at a 4' position of the xanthene ring structure.

12. The energy transfer dye according to claim 11 wherein the linker includes a $R_3X$ group where $R_3$ is a $C_{1-5}$ alkyl attached to the donor dye and X is selected from the group consisting of NH, sulfur and oxygen.

13. The energy transfer dye according to claim 11 wherein the linker includes a $R_3XC(O)R_4N$ group where $R_3$ is a $C_{1-5}$ alkyl attached to the donor dye, X is selected from the group consisting of NH, sulfur and oxygen, C(O) is a carbonyl group, and $R_4$ includes a carbon backbone which links the carbonyl carbon to the nitrogen.

14. The energy transfer dye according to claim 12 wherein $R_4$ includes a functional group selected from the group consisting of an alkene, diene, alkyne, a five and six membered ring having at least one unsaturated bond and a fused ring structure which is attached to the carbonyl carbon.

15. The energy transfer dye according to claim 10 wherein the donor dye is 5-carboxyfluorescein.

16. The energy transfer dye according to claim 10 wherein the acceptor dye is selected from the group consisting of 5-carboxy-X-rhodamine and Cy5.

17. The energy transfer dye according to claim 10 wherein the acceptor dye has the general structure

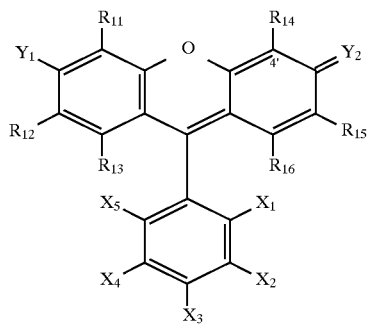

wherein:

$Y_1$ and $Y_2$ are each independently selected from the group consisting of hydroxyl, oxygen, iminium and amine;

$R_{11}$–$R_{16}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof;

$X_1$, $X_2$, $X_3$, $X_4$ and $X_5$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof; and one of $R_{11}$–$R_{16}$ and $X_1$–$X_5$ is the linker.

18. The energy transfer dye according to claim 17 wherein $X_3$ of the acceptor is the linker.

19. An energy transfer fluorescent dye comprising:

a donor dye which absorbs light at a first wavelength and emitting excitation energy in response, the donor dye having the general structure

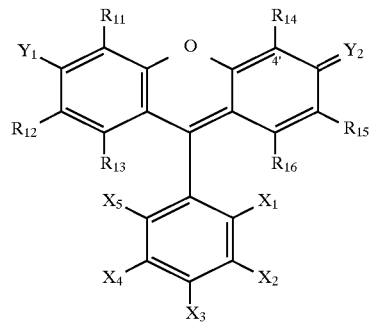

wherein:

$Y_1$ and $Y_2$ are each independently selected from the group consisting of hydroxyl, oxygen, iminium and amine, $R_{11}$–$R_{16}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof, and $X_1$, $X_2$, $X_4$ and $X5$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof;

an acceptor dye which is capable of absorbing the excitation energy emitted by the donor dye and fluorescing at a second wavelength in response, the acceptor dye having the general structure

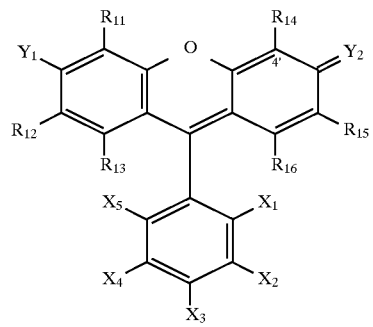

wherein:

$Y_1$ and $Y_2$ are each independently selected from the group consisting of hydroxyl, oxygen, iminium and amine, $R_{11}$–$R_{16}$ are each independently selected from the group consisting of hydrogen, fluorine, chlorine, bromine, iodine, carboxyl, alkyl, alkene, alkyne, sulfonate, amino, ammonium, amido, nitrile, alkoxy, phenyl, substituted phenyl, where adjacent substituents are taken together to form a ring, and combinations thereof, and $X_1$, $X_2$, $X_4$ and $X_5$ are each independently selected from the group consisting of hydrogen, fluorine, chlorine, bromine, iodine, carboxyl, alkyl, alkene, alkyne, sulfonate, amino, ammonium, amido, nitrile, alkoxy, where adjacent substituents are taken together to form a ring, and combinations thereof; and a linker forming the $X_3$ substituents of the donor and acceptor dyes.

20. The energy transfer dye according to claim 18 wherein the linker has a backbone attaching the donor to the acceptor which is less than 9 atoms in length.

21. The energy transfer dye according to claim 18 wherein the linker has the general formula $-R_5XC(O)R_6XC(O)-$ where $R_5$ and $R_6$ are each a $C_{1-4}$ alkyl, $C(O)$ is a carbonyl group and each X is selected from the group consisting of NH, sulfur and oxygen.

22. The energy transfer dye according to claim 18 wherein the linker has the general formula $-R_7XC(O)-$ where $R_7$ is an $C_{1-4}$ alkyl, $C(O)$ is a carbonyl group and X is selected from the group consisting of NH, sulfur and oxygen.

23. An energy transfer fluorescent dye selected from the group consisting of: 5TMR-B-CF, 5TMR-F-CF, 5TMR-P-CF, 5TMR-P-CF, 5TMR-A-CF, 5TMR-D-CF, 5TMR-N-CF, 5-ROX-CF, CY5-CF, 5TMR-gly-5AMF and 5TMR-5AMF.

24. A fluorescently labeled reagent comprising:
a reagent selected from the group consisting of a nucleoside, nucleoside monophosphate, nucleoside diphosphate and nuleoside triphosphate, modified to be attached to an energy transfer fluorescent dye; and
an energy transfer fluorescent dye attached to the reagent, the energy transfer fluorescent dye including
a donor dye with a xanthene ring structure, the donor dye absorbing light at a first wavelength and emitting excitation energy in response;
an acceptor dye which is capable of absorbing the excitation energy emitted by the donor dye and fluorescing at a second wavelength in response; and
a linker attaching the donor dye to the acceptor dye, the linker having a 4' end which includes a $R_1XC(O)R_2$ group where $R_1$ is a $C_{1-5}$ alkyl attached to a 4' ring position on the xanthene ring structure of the donor dye, X is selected from the group consisting of NH, sulfur and oxygen, $C(O)$ is a carbonyl group, and $R_2$ attaches the linker to the acceptor dye and includes a functional group which is attached to the carbonyl carbon selected from the group consisting of an alkene, diene, alkyne, a five and six membered ring having at least one unsaturated bond and a fused ring structure.

25. The fluorescently labeled reagent according to claim 24 wherein the donor dye is a member of a class of dyes selected from the group consisting of fluorescein, rhodamine and asymmetric benzoxanthene dyes.

26. The fluorescently labeled reagent according to claim 24 wherein the acceptor dye is a member of a class of dyes selected from the group consisting of xanthene, cyanine, phthalocyanine and squaraine.

27. The fluorescently labeled reagent according to claim 26 wherein the functional group attached to the carbonyl carbon is selected from the group consisting of cyclopentene, cyclohexene, cyclopentadione, cyclohexadiene, furan, thiofuran, pyrrole, isopyrole, isoazole, pyrazole, isoimidazole, pyran, pyrone, benzene, pyridine, pyridazine, pyrimidine, pyrazine, oxazine, indene, benzofuran, thionaphthene, indole and naphthalene.

28. The fluorescently labeled reagent according to claim 24 wherein the acceptor is a member of the xanthene class of dyes.

29. The fluorescently labeled reagent according to claim 26 wherein the reagent is selected from the group consisting of deoxynucleoside, deoxynucleoside monophosphate, deoxynucleoside diphosphate and deoxynucleoside triphosphate.

30. The fluorescently labeled reagent according to claim 29 wherein the deoxynucleotides are selected from the group consisting of deoxycytosine, deoxyadenosine, deoxyguanosine, and deoxythymidine.

31. The fluorescently labeled reagent according to claim 26 wherein the reagent is selected from the group consisting of dideoxynucleoside, dideoxynucleoside monophosphate, dideoxynucleoside diphosphate and dideoxynuloside triphosphate.

32. The fluorescently labeled reagent according to claim 31 wherein the dideoxynucleotides are selected from the group consisting of deoxycytosine, deoxyadenosine, deoxyguanosine, and deoxythymidine.

33. A fluorescently labeled reagent comprising:
a reagent selected from the group consisting of a nucleoside, nucleoside monophosphate, nucleoside diphosphate and nucleoside triphosphate, modified to be attached to an energy transfer fluorescent dye; and
an energy transfer fluorescent dye attached to the reagent, the energy transfer fluorescent dye including
a donor dye with a xanthene ring structure, the donor dye absorbing light at a first wavelength and emitting excitation energy in response;
an acceptor dye which is a member of a class of dyes selected from the group consisting of xanthene, cyanine, phthalocyanine and squaraine and is capable of absorbing the excitation energy emitted by the donor dye and fluorescing at a second wavelength in response, the acceptor having an emission maximum that is greater than about 600 nm or at least about 100 nm greater than the absorbance maximum of the donor dye; and
a linker attaching the donor dye to the acceptor dye which has a sufficiently short length that the acceptor dye absorbs substantially all of the excitation energy emitted by the donor dye.

34. The fluorescently labled reagent according to claim 33 wherein the linker is attached to the donor dye at a 4' position of the xanthene ring structure.

35. The fluorescently labeled reagent according to claim 34 wherein the linker includes a $R_3X$ group where $R_3$ is a $C_{1-5}$ alkyl attached to the donor dye and X is selected from the group consisting of NH, sulfur and oxygen.

36. The fluorescently labeled reagent according to claim 34 wherein the linker includes a $R_3XC(O)R_4N$ group where $R_3$ is a $C_{1-5}$ alkyl attached to the donor dye, X is selected from the group consisting of NH, sulfur and oxygen, $C(O)$ is a carbonyl group, and $R_4$ includes a carbon backbone which links the carbonyl carbon to the nitrogen.

37. The fluorescently labeled reagent according to claim 33 wherein the reagent is selected from the group consisting of deoxynucleoside, deoxynucloside monophosphate, deoxynucloside diphosphate and deoxynucleoside triphosphate.

38. The fluorescently labeled reagent according to claim 37 wherein the deoxynucleotides are selected from the group consisting of deoxycytosine, deoxyadenosine, deoxyguanosine, and deoxythymidine.

39. The fluorescently labeled reagent according to claim 36 wherein the reagent is selected from the group consisting of dideoxynucleoside, dideoxynucleoside monophosphate, dideoxynucleotide diphosphate and dideoxynucleoside triphosphate.

40. The fluorescently labeled reagent according to claim 39 wherein the dideoxynucleotides are selected from the group consisting of deoxycytosine, deoxyadenosine, deoxyguanosine, and deoxythymidine.

41. A fluorescently labeled oligonucleotide primer comprising:
an oligonucleotide; and
an energy transfer fluorescent dye attached to the oligonucleotide, the energy transfer fluorescent dye including a donor dye with a xanthene ring structure, the donor dye absorbing light at a first wavelength and emitting excitation energy in response;

an acceptor dye which is capable of absorbing the excitation energy emitted by the donor dye and fluorescing at a second wavelength in response; and a linker attaching the donor dye to the acceptor dye, the linker having a 4' end which includes a $R_1XC(O)R_2$ group where $R_1$ is a $C_{1-5}$ alkyl attached to 4' ring position on the xanthene ring structure of the donor dye, X is selected from the group consisting of NH, sulfur and oxygen, C(O) is a carbonyl group, and $R_2$ attaches the linker to the acceptor dye a includes a functional group which is attached to the carbonyl carbon selected from the group consisting of an alkene, diene, alkyne, a five and six membered ring having at least one unsaturated bond and a fused ring structure.

42. The fluorescently labeled oligonucleotide primer according to claim 41 wherein the donor dye has a fluorescein or rhodamine ring structure.

43. The fluorescently labeled oligonucleotide primer according to claim 41 wherein the acceptor dye is a member of a class of dyes selected from the group consisting of xanthene, cyanine, phthalocyanine and squaraine dyes.

44. The fluorescently labeled oligonucleotide primer according to claim 41 wherein $R_2$ includes a five or six membered ring which is selected from the group consisting of cyclopentene, cyclohexene, cyclopentadiene, cyclohexadiene, furan, thiofuran, pyrrole, isopyrole, isoazole, pyrazole, isoimidazole, pyran, pyrone, benzene, pyridine, pyridazine, pyrimidine, pyrazine, oxazine.

45. The fluorescently labeled oligonucleotide primer according to claim 41 wherein the acceptor is a member of the xanthene class of dyes.

46. A fluorescently labeled oligonucleotide primer comprising:

an oligonucleotide; and an energy transfer fluorescent dye attached to the oligonucleotide, the energy transfer fluorescent dye including a donor dye with a xanthene ring structure, the donor dye absorbing light at a first wavelength and emitting excitation energy in response, an acceptor dye which is a member of a class of dyes selected from the group consisting of xanthene, cyanine, phthalocyanine and squaraine and is capable of absorbing the excitation energy emitted by the donor dye and fluorescing at a second wavelength in response, the acceptor having an emission maximum that is greater than about 600 nm or at least about 100 nm greater than the absorbance maximum of the donor dye; and a linker attaching the donor dye to the acceptor dye which has a sufficiently short length that the acceptor dye absorbs substantially all of the excitation energy emitted by the donor dye.

47. The fluorescently labeled reagent according to claim 46 wherein the linker is attached to the donor dye at a 4' position of the xanthene ring structure.

48. The fluorescently labeled reagent according to claim 47 wherein the linker includes a $R_3X$ group where $R_3$ is a $C_{1-5}$ alkyl attached to the donor dye and X is selected from the group consisting of NH, sulfur and oxygen.

49. The fluorescently labeled reagent according to claim 47 wherein the linker includes a $R_3XC(O)R_4N$ group where $R_3$ is a $C_{1-5}$ alkyl attached to the donor dye, X is selected from the group consisting of NH, sulfur and oxygen, C(O) is a carbonyl group, and $R_4$ includes a carbon backbone which links the carbonyl carbon to the nitrogen.

50. A method for sequencing a nucleic acid sequence comprising:

forming a mixture of extended labeled primers by hybridizing a nucleic acid sequence with a fluorescently labeled oligonucleotide primer in the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is incorporated which terminates extension of the primer;

separating the mixture of extended primers; and determining the sequence of the nucleic acid sequence by fluorescently measuring the mixture of extended primers formed;

the fluorescently labeled oligonucleotide primer including an oligonucleotide sequence complementary to a portion of the nucleic acid sequence being sequenced, and an energy transfer fluorescent dye attached to the oligonucleotide, the energy transfer fluorescent dye including a donor dye with a xanthene ring structure the donor dye absorbing light at a first wavelength and emitting excitation energy in response;

an acceptor dye which is capable of absorbing the excitation energy emitted by the donor dye and fluorescing at a second wavelength in response; and a linker attaching the donor dye to the acceptor dye, the linker having a 4' end which includes a $R_1XC(O)R_2$ group where $R_1$ is a $C_{1-5}$ alkyl attached to a 4' ring position on the xanthene ring structure of the donor dye, X is selected from the group consisting of NH, sulfur and oxygen, C(O) is a carbonyl group, and $R_2$ atttaches the linker to the acceptor dye and includes a functional group which is attached to the carbonyl carbon selected from the group consisting of an alkene, diene, alkyne, a five and six membered ring having at least one unsaturated bond and a fused ring structure.

51. A method for sequencing a nucleic acid sequence comprising:

forming a mixture of extended labeled primers by hybridizing a nucleic acid sequence with a fluorescently labeled oligonucleotide primer In the presence of deoxynucleoside triphosphates, at least one dideoxynucleoside triphosphate and a DNA polymerase, the DNA polymerase extending the primer with the deoxynucleoside triphosphates until a dideoxynucleoside triphosphate is Incorporated which terminates extension of the primer;

separating the mixture of extended primers; and determining the sequence of the nucleic acid sequence by fluorescantly measuring the mixture of extended primers formed;

the fluorescently labeled oligonucleotide primer including an oligonucleotide sequence complementary to a portion of the nucleic acid sequence being sequenced, and an energy transfer fluorescent dye attached to the oligonucleotide, the energy transfer fluorescent dye including a donor dye with a xanthene ring structure, the donor dye absorbing light at a first wavelength and emitting excitation energy in response, an acceptor dye which is a member of a class of dyes selected from the group consisting of xanthene, cyanine, phthalocyanine and squaraine and is capable of absorbing the excitation energy emitted by the donor dye and fluorescing at a second wavelength in response, the acceptor having an emission maximum that is greater than about 600 nm or at least about 100 nm greater than the absorbance maximum of the donor dye; and a linker attaching the donor dye to the acceptor dye which has a sufficiently short length that the acceptor dye absorbs substantially all of the excitation energy emitted by the donor dye.

52. A method for sequencing a nucleic acid sequence comprising:

forming a mixture of extended primers by hybridizing a nucleic acid sequence with a primer in the presence of deoxynucleoside triphosphates, at least one fluorescently labeled dideoxynucleoside triphosphate and a DNA polymerase, the DNA polymerase extending the primer with the deoxyucteoside triphosphates until a fluorescently labeled dideoxynucleoside triphosphate is incorporated onto the extended primer which terminates extension of the primer;

separating the mixture of extended primers; and determining the sequence of the nucleic acid sequence by detecting the fluorescently labeled dideoxynucleotide attached to the separated mixture of extended primers;

the fluorescently labeled dideoxynucleotide triphosphate including a dideoxynucleotide triphosphate, and an energy transfer fluorescent dye attached to the dideoxynucleotide triphosphate, the dye including a donor dye with a xanthene ring structure, the donor dye absorbing light at a first wavelength and emitting excitation energy in response;

an acceptor dye which is capable of absorbing the excitation energy emitted by the donor dye and fluorescing at a second wavelength in response; and a linker attaching the donor dye to the acceptor dye, the linker having a 4' end which includes a $R_1XC(O)R_2$ group where $R_1$ is a $C_{1-5}$ alkyl attached to a 4' ring position on the xanthene ring structure of the donor dye, X is selected from the group consisting of NH, sulfur and oxygen, C(O) is a carbonyl group, and $R_2$ attaches the linker to the acceptor dye and includes a functional group which is attached to the carbonyl carbon selected from the group consisting of an alkene, diene, alkyne, a five and six membered ring having at least one unsaturated bond and a fused ring structure.

53. A method for sequencing nucleic acid sequence comprising:

forming a mixture of extended primers by hybridizing a nucleic acid sequence with a primer in the presence of deoxynucleoside triphosphates, at least one fluorescently labeled dideoxynucleoside triphosphate and a DNA polymerase, the DNA polymerase extending the primer with the deoxynucleoside triphosphates until a fluorescently labeled dideoxynucleoside triphosphate is incorporated onto the extended primer which terminates extension of the primer;

separating the mixture of extended primers; and determining the sequence of the nucleic acid sequence by detecting the fluorescently labeled dideoxynucleotide attached to the separated mixture of extended primers;

the fluorescently labeled dideoxynucleotide triphosphate including a dideoxynucleotide triphosphate, and an energy transfer fluorescent dye attached to the dideoxynucleotide triphosphate, the dye including a donor dye with a xanthene ring structure, the donor dye absorbing light at a first wavelength and emitting excitation energy in response, an acceptor dye which is a member of a class of dyes selected from the group consisting of xanthene, cyanine, phthalocyanine and squaraine and is capable of absorbing the excitation energy emitted by the donor dye and fluorescing at a second wavelength in response, the acceptor having an emission maximum that is greater than about 600 nm or at least about 100 nm greater than the absorbance maximum of the donor dye; and a linker attaching the donor dye to the acceptor dye which has a sufficiently short length that the acceptor dye absorbs substantially all of the excitation energy emitted by the donor dye.

54. An energy transfer fluorescent dye comprising:

a donor dye which has a carboxy fluorescein ring structure, the donor dye absorbing light at a first wavelength and emitting excitation energy in response;

an acceptor dye which has a 5-carboxy-X-rhodamine ring structure and is capable of absorbing the excitation energy emitted by the donor dye and fluorescing at a second wavelength in response; and a linker attaching the donor dye to the acceptor dye which has a sufficiently short length that the acceptor dye absorbs substantially all of the excitation energy emitted by the donor dye.

55. A fluorescently labeled reagent comprising;

a reagent selected from the group consisting of a nucleoside, nucleoside monophosphate, nucleoside diphosphate and nucleoside triphosphate, modified to be attached to an energy transfer fluorescent dye; and an energy transfer fluorescent dye attached to the reagent, the energy transfer fluorescent dye including a donor dye which has a carboxy fluorescein ring structure, the donor dye absorbing light at a first wavelength and emitting excitation energy in response;

an acceptor dye which has a 5-carboxy-X-rhodamine ring structure and is capable of absorbing the excitation energy emitted by the donor dye and fluorescing at a second wavelength in response; and a linker attaching the donor dye to the acceptor dye which has a sufficiently short length that the acceptor dye absorbs substantially al of the excitation energy emitted by the donor dye.

56. A fluorescently labeled oligonucleotide primer comprising:

oliganucleotide; and an energy transfer fluorescent dye attached to the oligonucleotide, the energy transfer fluorescent dye including a donor dye which has a carboxy fluorescein ring structure, the donor dye absorbing light at a first wavelength and emitting excitation energy in response;

an acceptor dye which has a 5-carboxy-X-rhodamine ring structure and is capable of absorbing the excitation energy emitted by the donor dye and fluorescing at a second wavelength in response; and a linker attaching the donor dye to the acceptor dye which has a sufficiently short length that the acceptor dye absorbs substantially all of the excitation energy emitted by the donor dye.

57. The energy transfer fluorescent dye according to claim 10 wherein the acceptor dye has a Cy5 ring structure.

58. The fluorescently labeled reagent according to claim 33 wherein the acceptor dye has a Cy5 ring structure.

59. The fuorescently labeled oligonucleotide primer according to claim 46 wherein the acceptor dye has a Cy5 ring structure.

* * * * *